(12) United States Patent
Kruckow et al.

(10) Patent No.: US 9,581,607 B2
(45) Date of Patent: Feb. 28, 2017

(54) TEST STATION AND METHOD FOR TESTING FLUIDIC COMPONENTS

(71) Applicant: FRAUNHOFER-GESELLSCHAFT ZUR FOERDERUNG DER ANGEWANDTEN FORSCHUNG E.V., Munich (DE)

(72) Inventors: Juergen Kruckow, Munich (DE); Sebastian Kibler, Munich (DE); Martin Richter, Munich (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 483 days.

(21) Appl. No.: 14/078,424

(22) Filed: Nov. 12, 2013

(65) Prior Publication Data

US 2014/0069214 A1  Mar. 13, 2014

Related U.S. Application Data

(63) Continuation of application No. PCT/EP2011/059602, filed on Jun. 9, 2011.

(30) Foreign Application Priority Data

May 12, 2011 (WO) ................. PCT/EP2011/057671

(51) Int. Cl.
| G01N 35/00 | (2006.01) |
| B01L 3/00 | (2006.01) |
| B01L 9/00 | (2006.01) |

(52) U.S. Cl.
CPC ........ *G01N 35/00* (2013.01); *B01L 3/502707* (2013.01); *B01L 3/502715* (2013.01); *B01L 9/527* (2013.01); *B01L 2200/023* (2013.01); *B01L 2200/025* (2013.01); *B01L 2200/027* (2013.01); *B01L 2200/143* (2013.01); *B01L 2300/0645* (2013.01); *B01L 2400/0415* (2013.01); *B01L 2400/0487* (2013.01); *G01N 35/00623* (2013.01)

(58) Field of Classification Search
None
See application file for complete search history.

(56) References Cited

U.S. PATENT DOCUMENTS

| 4,864,229 | A | * | 9/1989 | Lauks et al. ............. 324/750.03 |
| 5,163,313 | A | * | 11/1992 | Haas et al. ........................ 73/41 |
| 5,668,307 | A | * | 9/1997 | Wade ............................. 73/40.7 |
| 7,361,946 | B2 | * | 4/2008 | Johnson et al. .............. 257/253 |
| 7,461,535 | B2 | * | 12/2008 | Huang et al. ................. 73/1.01 |
| 8,053,267 | B2 | * | 11/2011 | Vaganov ......................... 438/53 |

(Continued)

*Primary Examiner* — Robert R Raevis
(74) *Attorney, Agent, or Firm* — Michael A. Glenn; Perkins Coie LLP

(57) ABSTRACT

A test station for testing at least one of fluidic component arranged on a substrate, each fluidic component having a fluidic port, comprises a carrier device for holding the substrate with the at least one fluidic component, a connecting device for fluidically connecting the fluidic port of the at least one fluidic component located in a testing position to a first adapter element of the connecting device, and a displacement device configured to displace the substrate and the connecting device relative to each other, and to bring the substrate into the testing position.

23 Claims, 11 Drawing Sheets

(56) References Cited

U.S. PATENT DOCUMENTS

| | | |
|---|---|---|
| 8,372,674 B2 * | 2/2013 | Cobianu et al. ............... 438/49 |
| 2003/0017085 A1 | 1/2003 | Kercso et al. |
| 2003/0229459 A1 | 12/2003 | Li et al. |
| 2004/0020268 A1 * | 2/2004 | Hotta ............................ 73/40.7 |
| 2006/0150385 A1 | 7/2006 | Gilligan et al. |
| 2009/0134522 A1 * | 5/2009 | Smith et al. .................. 257/769 |
| 2013/0074584 A1 * | 3/2013 | Graham ........................... 73/41 |

* cited by examiner

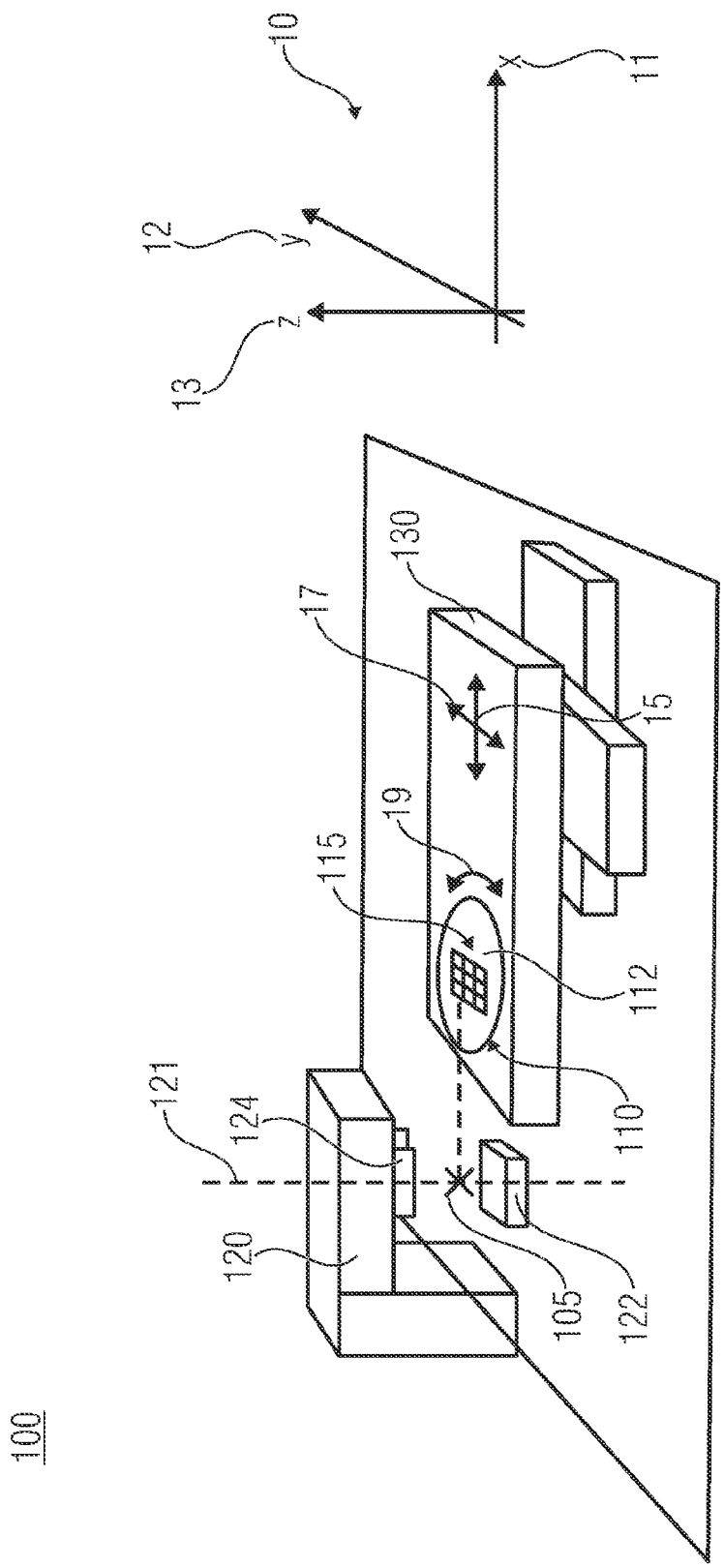

TEST STATION AND METHOD FOR TESTING FLUIDIC COMPONENTS

CROSS-REFERENCE TO RELATED APPLICATIONS

This application is a continuation of copending International Application No. PCT/EP2011/059602, filed Jun. 9, 2011, which is incorporated herein by reference in its entirety, and additionally claims priority from PCT/EP2011/057671, filed May 12, 2011, which is also incorporated herein by reference in its entirety.

BACKGROUND OF THE INVENTION

The present invention relates to a test station and a method for testing (micro) fluidic components, e.g. fluidic MEMS components or elements, e.g. micro pumps, micro valves, micro-reactors, etc. In particular, the present invention relates to an automatic test of fluidic components on wafer level.

To date, only a few MEMS (MEMS=micro elector mechanical system) components, such as pressure sensors, gyroscopes and acceleration sensors can be found in large quantities on the world market. Fluidic MEMS components in silicon (Si), however, such as micro fluidic chips, micro dispensers, micro pumps and micro valves are only available in small quantities on the market. Limiting obstacles for entering the market with large quantities of such fluidic Si devices are the relatively high manufacturing costs.

As fluidic MEMS components are, up to now, in only relatively small quantities on the market, industrial producers of test devices are, so far, not willing to invest in device developments, as the quantities of devices to be possibly sold will hardly pay off investment costs. Hence, the development of MEMS test devices can still be considered as a niche application. In particular, a developed test station, beside a diaphragm testing unit for pressure sensor chips, an automatic fluidic MEMS device tester on wafer level, is not known on the market.

In the art, common characterization methods for fluidic components are known in the form of manual tests or based on half automatic test devices having specific test adapters for individual chips. Fluidic devices are, for example, first inserted into such specific adapters in an unpackaged manner and are then tested. However, in this case, the fluidic devices will subsequently have to be tested again after packaging, since chip assembly can include sources of error, which represents a disadvantage. Moreover, mounting the chip first into the package, wherein in many cases mounting is performed by means of an adhesive step firmly connecting the adhered chips with the package and hence preventing reuse of the package, and only then testing after chip packaging has some significant disadvantages and causes additional costs since chips that are defective or insufficient with regard to their specification are necessitated to be disposed of after the test, including the packaging. Therefore, the methods described above are disadvantageous in that they are very time-consuming and, hence, costly.

Thus, a general disadvantage of known methods for the characterization of fluidic MEMS components is that these methods are time-consuming and not cost-effective.

SUMMARY

According to an embodiment, a test station for testing at least one fluidic component arranged on a substrate, each fluidic component having a fluidic port, may have: a carrier device for holding the substrate with the at least one fluidic component; a connecting device for fluidically connecting the fluidic port of the at least one component located in a testing position to a first adapter element of the connecting device; and a displacement device configured to displace the substrate and the connecting device relative to each other, and to bring the substrate into the testing position.

According to another embodiment, a method for testing at least one fluidic component arranged on a substrate, each fluidic component having a fluidic port, wherein the substrate with the at least one fluidic component is fixed in a holder, may have the steps of: bringing the substrate into a testing position; and in the testing position, fluidically connecting the fluidic port of the at least one fluidic components to a first adapter element.

Another embodiment may have a computer program having a program code for performing the above method for testing when the computer program is executed on a computer.

According to another embodiment, a wafer level test station for testing at least one fluidic component arranged on a wafer, each fluidic component having a fluidic port, may have: a carrier device for holding the wafer with the at least one fluidic component; a connecting device for fluidically connecting the fluidic port of the at least one component located in a testing position to a first adapter element of the connecting device; and a displacement device configured to displace the wafer and the connecting device relative to each other, and to bring the wafer into the testing position; wherein the connecting device further has a second adapter element arranged in an opposing position to the first adapter element with respect to the wafer in the testing position, wherein at least one of the first adapter element and the second adapter element is configured to be displaced towards the other element, so that the first adapter element and the second adapter element are brought into contact with the at least one fluidic component from opposite sides; wherein the connecting device is configured to displace the at least one of the first adapter element and the second adapter element towards the other element along a linear axis, the linear axis extending vertically and centrically through the first adapter element and the second adapter element; wherein the displacement device is configured to bring, in a first phase, a first fluidic component into the testing position, so that, in the first phase, the fluidic port of the first fluidic component is fluidically connected to the first adapter element and to bring, in a second phase, a second fluidic component into the testing position, so that, in the second phase, the fluidic port of the second fluidic component is fluidically connected to the first adapter element; wherein the first adapter element has a fluidic contact element, wherein the first adapter element is configured to fluidically connect the fluidic port of the fluidic component from a first side of the fluidic component; wherein the second adapter element has a fluidic contact element or an electrical contact element, wherein the second adapter element is configured to fluidically or electrically contact a further fluidic port or an electrical connecting port of the fluidic component from a second side of the fluidic component, wherein the second side of the fluidic component is opposite to the first side of the fluidic component; wherein the first adapter element and the second adapter element are configured to fluidically connect and/or electrically contact the fluidic component from opposite sides.

According to still another embodiment, a wafer level test station for simultaneously testing a plurality of fluidic components arranged on a wafer, each fluidic component having a fluidic port, may have: a carrier device for holding the wafer with the at least one fluidic component; a connecting device for fluidically connecting the fluidic ports of plurality of fluidic components located in a testing position to a first adapter element of the connecting device; and a displacement device configured to displace the wafer and the connecting device relative to each other, and to bring the wafer into the testing position; wherein the connecting device further has a second adapter element arranged in an opposing position to the first adapter element with respect to the wafer in the testing position, wherein at least one of the first adapter element and the second adapter element is configured to be displaced towards the other element, so that the first adapter element and the second adapter element are brought into contact with the plurality of fluidic components from opposite sides; wherein the connecting device is configured to displace the at least one of the first adapter element and the second adapter element towards the other element along a linear axis, the linear axis extending vertically and centrically through the first adapter element and the second adapter element; wherein the displacement device is configured to bring, in a first phase, a first group of fluidic components into the testing position, so that, in the first phase, fluidic ports of the first group of fluidic components are fluidically connected to the first adapter element and to bring, in a second phase, a second group of fluidic components into the testing position, so that, in the second phase, fluidic ports of the second group of fluidic components are fluidically connected to the first adapter element; wherein the first adapter element has a fluidic contact element, wherein the first adapter element is configured to fluidically connect the fluidic port of the fluidic component from a first side of the fluidic component; wherein the second adapter element has a fluidic contact element or an electrical contact element, wherein the second adapter element is configured to fluidically or electrically contact a further fluidic port or an electrical connecting port of the fluidic component from a second side of the fluidic component, wherein the second side of the fluidic component is opposite to the first side of the fluidic component; wherein the first adapter element and the second adapter element are configured to fluidically connect and/or electrically contact the fluidic component from opposite sides.

According to an embodiment of the present invention, a test station for testing at least one or a plurality of active or passive fluidic or micro-fluidic components arranged on a substrate or wafer, each of the fluidic components comprising a fluidic port, comprises a carrier device, a connecting device and a displacement device. The carrier device is configured for holding the substrate with the fluidic components. The connecting device is configured for fluidically connecting the fluidic port of the at least one fluidic component located in a testing position to a first adapter element of the connecting device. The displacement device is configured to displace the substrate and the connecting device relative to each other, and to bring the substrate into the testing position.

The present invention is based on the finding that the above-mentioned more efficient testing can be realized if the substrate is brought into a testing position and if, in the testing position, the fluidic port of the at least one fluidic component is fluidically connected to a first adapter element and a testing process is performed with the fluidic component fluidically connected to the first adapter. After completion of this testing process, a further at least one fluidic component on the substrate can be immediately brought in the testing position and, in the testing position, the fluidic port of the further fluidic component is fluidically connected to the first adapter element and a subsequent testing process can be performed. Thus, the fluidic ports of a plurality of fluidic components can be fluidically connected to the first adapter element and a testing process is performed with the fluidic components fluidically connected to the first adapter. After completion of this testing process, a further plurality of fluidic components on the substrate can be immediately brought in the testing position and, in the testing position, the fluidic ports of the further plurality of fluidic components are fluidically connected to the first adapter element and a subsequent testing process can be performed. This allows to test different fluidic components immediately one after another, or to simultaneously test a plurality of fluidic components. In this way, it is possible to avoid a time-consuming and costly process procedure, thereby realizing an improved concept for testing at least one or a plurality of fluidic components in a more efficient manner.

Thus, embodiments of the concept of testing a plurality of fluidic components provide measurement or testing methods including sequential (or consecutive) processing of individual fluidic components on a substrate or concurrent (or simultaneous) processing of a several fluidic components on a substrate, and also provides a test station for performing the inventive measurement and testing methods.

According to a further embodiment, the test station further comprises a sensor device. The sensor device is configured to measure a fluidic characteristic of the fluidic components to be tested. Such fluidic or micro-fluidic components are, for example, micro pumps, valves, mixers, drop dispensers, nozzles or micro reactors, which may be implemented as so-called MEMS elements. By using the sensor device, it is possible to fluidically characterize the fluidic component to be tested. The sensor device can, for example, be a flow sensor, a pressure sensor, an optical sensor, an electrical sensor or a force sensor for sensing a flow characteristic, a pressure characteristic, an optical characteristic, a mechanical characteristic, an electrical (e.g. impedance) characteristic or a force characteristic of the fluidic component to be tested.

According to a further embodiment, the connecting device further comprises a second adapter element arranged in an opposing position to the first adapter element with respect to the substrate in the testing position. Here, the first adapter element and the second adapter element are configured to be displaced towards each other. As a result, the first adapter element and the second adapter element can be brought into contact with the at least one of the fluidic components from opposite sides.

In further embodiments, the first adapter element or the second adapter element comprises a contact element selected from a group consisting of a fluidic contact element, an electrical contact element and a mechanical contact element. This allows to fluidically connect and/or electrically or mechanically contact the fluidic component to be tested from opposite sides in a flexible way. The fluidic contact element and/or the connecting device can be spring suspended in order to limit the mechanical load or to avoid a mechanical overload or overstressing of the fluidic component(s) to be tested or of the substrate having arranged thereon the fluidic component(s).

According to a further embodiment, a method for testing at least one or a plurality of fluidic components comprises holding the substrate with the fluidic components, bringing the substrate into a testing position and, in the testing position, fluidically connecting the fluidic port of the at least one fluidic component to a first adapter element.

In further embodiments, the method further comprises measuring a fluidic characteristic of the fluidic component to be tested.

BRIEF DESCRIPTION OF THE DRAWINGS

In the following, embodiments of the present invention will be explained with reference to the accompanying drawings, in which:

FIG. 1b shows a schematic top view of the embodiment of the test station in accordance with FIG. 1a;

FIG. 1c shows a schematic perspective view of the embodiment of the test station in accordance with FIG. 1a;

FIG. 2b shows a schematic cross-sectional view of an embodiment of an fluidic component configured to be contacted by the embodiments of the two opposing adapter elements in accordance with FIG. 2a;

DETAILED DESCRIPTION OF THE INVENTION

Figure 1A:
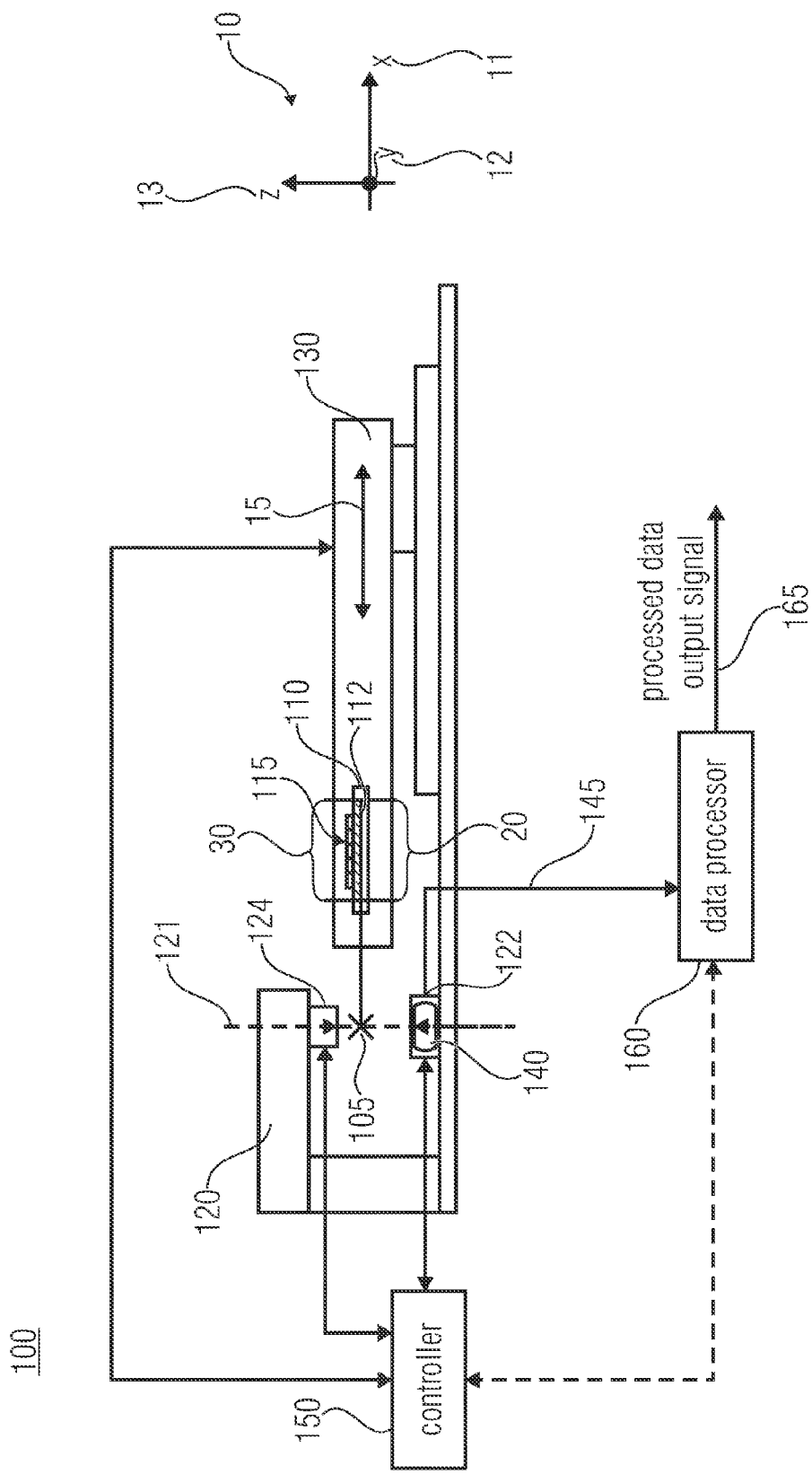
FIG. 1a shows a schematic cross-sectional view of an embodiment of a test station for testing a plurality of fluidic components.

Before discussing the present invention in further detail using the drawings, it is pointed out that in the figures, identical elements, elements having the same function or the same effect are provided with same reference numerals so that the description of these elements and the functionality thereof illustrated in the different embodiments is mutually exchangeable or may be applied to one another in the different embodiments.

FIG. 1a shows a schematic cross-sectional view of an embodiment of a test station 100 for testing at least one or a plurality 115 of fluidic or micro fluidic components (elements), e.g. micro pumps, micro valves, micro-reactors, pressure sensors, gyroscopes, acceleration sensors, nozzles etc. which may be implemented as MEMS elements. As shown in FIG. 1a, the plurality 115 of fluidic components is arranged on a substrate 112. Here, each of the fluidic components may comprise at least one (accessible) fluidic port. A respective fluidic component of the plurality 115 of fluidic components is, for example, a micro pump, a micro valve, a mixer or a drop dispenser. Referring to the embodiment of FIG. 1a, the test station 100 comprises a carrier device 110, a connecting device 120 and a displacement device 130. The carrier device 110 is configured for holding the substrate or wafer 112 with the fluidic component(s) 115. The connecting device 120 may be configured for fluidically connecting the fluidic port of the at least one fluidic component located in a testing position 105 to a first adapter element 122 of the connecting device 120. The displacement device 130 may be configured to displace the substrate 112 and the connecting device 120 relative to each other and to bring the substrate 112 into the testing position 105.

For example, the substrate is brought into a testing position and, in the testing position, the fluidic port of the at least one fluidic component is fluidically connected to the first adapter element and a testing process is performed with the fluidic component fluidically connected. After completion of this testing process, a further fluidic component on the substrate can be immediately brought in the testing position and, in the testing position, the fluidic port of the further fluidic component is fluidically connected to the first adapter element and a subsequent testing process can be performed. This allows to test several fluidic components immediately one after another, or to simultaneously test several fluidic components, wherein the fluid components are arranged on a substrate or wafer.

As exemplarily depicted in FIG. 1a, the testing position 105 is essentially located between the first adapter element 122 and a second adapter element 124 of the connecting device 120, for example, on a linear axis 121 extending vertically and centrically through the first and the second adapter elements 122, 124. The connecting device 120 of the test station 100 can, for example, be fixed with respect to the testing position 105 or linear axis 121. In the embodiment of FIG. 1a, the displacement device 130 may be configured as an x,y-table. The x,y-table may be configured to displace the substrate 112 in an x,y-plane extending through the testing position 105, wherein the x,y-plane is defined by the x-axis 11 and the y-axis 12 of a coordinate system 10. It is depicted in FIG. 1a that the substrate 112 with the fluidic components 115 is essentially displaced along a direction 15 parallel to the x-axis 11 by the displacement device 130 of the test station 100. Therefore, according to the embodiment of FIG. 1a, the displacement device 130 may be configured to bring the substrate 112 into the testing position 105, while the connecting device 120 may be configured to displace at least one of the first and the second adapter elements 122, 124 towards the other element (or the first and the second adapter elements 122, 124 towards each other) along the linear axis 121 parallel to the z-axis 13. In the testing position 105, the at least one of the first and the second adapter elements 122, 124 can, thus, be brought into contact with at least one of the fluidic components from one side (or the first and the second adapter elements 122, 124 can be brought into contact with the at least one fluidic component from opposing sides or surfaces).

It is to be noted that for this purpose, it is necessitated that the at least one fluidic component is accessible from one side or both sides thereof. In particular, a lower region 20, an upper region 30 or both regions 20, 30 below and/or above the at least one fluidic component may represent a recess region in the carrier device 110 and the displacement device 130, such that the at least one fluidic component will be accessible by the first adapter element 122 from below or the second adapter element 124 from above (with respect to the geometrical representation in FIG. 1a).

In the embodiment of FIG. 1a, the first adapter element 122 may be fixed in the testing position 105, so that its upper end lies in (or is flush with) the x,y-plane extending through the testing position 105. In addition, a lower end of the at least one fluidic component may be aligned to be in (or is flush with) the same x,y-plane as the upper end of the first adapter element 122. In this case, it is only necessitated to displace the second adapter element 124 along the linear axis 121 for bringing the first and the second adapter elements 122, 124 into contact with the at least one fluidic component.

Similarly, the second adapter element 124 may be fixed in the testing position 105, so that its lower end lies in (or is flush with) the x,y-plane extending through the testing position 105. In addition, an upper end of the at least one fluidic component may be aligned to be in (or is flush with) the same x,y-plane as the lower end of the second adapter element 124. In this case, it is only necessitated to displace the first adapter element 122 along the linear axis 121 for bringing the first and the second adapter elements 122, 124 into contact with the at least one fluidic component.

Therefore, according to the embodiment of FIG. 1a, the upper end of the first adapter element 122 and the lower end of the at least one fluidic component may be aligned to be in the same x,y-plane or, alternatively, the lower end of the second adapter element 124 and the upper end of the at least one fluidic component may be aligned to be in the same x,y-plane, so that only the respective other element needs to be displaceable along the linear axis 121 for bringing both sides of the at least one fluidic component into contact with the first and the second adapter elements 122, 124.

Referring to the embodiment of FIG. 1a, the test station 100 may further comprise a sensor device 140 configured to measure a fluidic characteristic of the fluidic component to be tested. As shown in FIG. 1a, the sensor device 140 of the test station 100 can, for example, be integrated into the first adapter element 122 of the connecting device 120. In the testing position, where the fluidic port of the at least one fluidic component is fluidically connected to the first adapter element 122, the sensor device 140 may be placed inside a fluidic line of the first adapter element 122 which is in fluidic contact with the fluidic port of the fluidic component. In this way, the sensor device 140 integrated into the first adapter element 122 can be employed to measure the fluidic characteristic of the fluidic component to be tested.

According to embodiments of the present invention, the sensor device 140 of the test station 100 may comprise a flow sensor, a pressure sensor, an electrical sensor or an optical sensor or a force sensor for sensing a flow characteristic, a pressure characteristic, an optical characteristic, a mechanical characteristic, an electrical characteristic or a force characteristic of the fluidic component to be tested.

It is, furthermore, illustrated in FIG. 1a that the test station 100 may comprise a controller 150 and a data processor 160. In embodiments, the controller 150 may be configured to control the displacement device 130 to perform a displacement of the substrate 112 and the connecting device 120 relative to each other. By such a displacement, it is possible to fluidically connect, in the testing position 105, the fluidic port of the fluidic component to be tested to the first adapter element 122. Here, it is to be noted that according to some embodiments, the displacement device 130 controlled by the controller 150 may be configured to move the carrier device 110 carrying the substrate 112 with the fluidic component or the connecting device 120 comprising the first adapter element 122 or both (i.e., the carrier device 110 and the connecting device 120), so that the substrate 112 will be brought into the testing position 105.

In embodiments described above with regard to FIG. 1a, the control of the displacement may be performed over a unidirectional or bidirectional communication as indicated by the double arrow.

In further embodiments, the controller 150 may be configured to control the first or the second adapter element 122, 124 to be displaced along the linear axis 121 in the z-direction 13.

In yet further embodiments, the controller 150 may be configured to control the sensor device 140 which is, for example, integrated into the first adapter element 122, to perform a measurement of the fluidic characteristic of the fluidic component to be tested, so as for obtaining a sensor device output signal 145.

In the embodiment of FIG. 1a, the data processor 160 may be configured for processing the sensor device output signal 145 to obtain a processed data output signal 165 representing the fluidic characteristic.

According to further embodiments, the controller 150 and the data processor 160 may communicate and exchange data by using an unidirectional or bidirectional communication as indicated by the dashed line in FIG. 1a.

Referring to the embodiment of FIG. 1a, the connecting device 120 may further comprise a second adapter element 124 arranged in an opposing position to the first adapter element 122 with respect to the substrate 112 in the testing position 105. In particular, the first adapter element 122 and the second adapter element 124 are configured to be displaced towards each other, thereby allowing to bring the first adapter element 122 and the second adapter element 124 into contact with at least one of the fluidic components from opposite sides. The fluidic contact element and/or the connecting device can be spring suspended in order to limit the mechanical load or to avoid a mechanical overload or overstressing of the fluidic component(s) to be tested or of the substrate having arranged thereon the fluidic component(s).

According to a further embodiment of the present invention, the first adapter element 122 may be configured for fluidically contacting fluidic ports of each of the fluidic components simultaneously. In other words, all of the fluidic components 115 arranged on the substrate 112 may be fluidically contacted simultaneously.

FIG. 1 *b* shows a schematic top view of the embodiment of the test station in accordance with FIG. 1*a*. In the top view of FIG. 1 *b*, it is exemplarily depicted that the carrier device 110 may be configured as a ring-shaped carrier or receptacle. The ring-shaped receptacle is, for example, rotatable with respect to a rotational axis which is parallel to the z-axis 13 along a rotational direction 19.

The carrier device 110 of FIG. 1 *b* may comprise fixing elements for manually or automatically fixing the substrate 112 or wafer to the carrier device 110. For example, the fixing elements may be in the form of a clamping frame configured to clamp the substrate 112 or wafer along its outer perimeter into the carrier device 110.

In some embodiments, the substrate or wafer can be fixed by a grid-like structure which may be part of the carrier or receptacle. The grid-like structure may be opened or at least one side of it may be foldable with respect to the rotatable mounted carrier device 110, such that the substrate or wafer can be received by the grid-like structure.

In further embodiments, if for example only an optical inspection of the placing (i.e. the location) or of the dimensions of the fluidic components is to be performed, the substrate or wafer can be fixed in a transparent holder which, in turn, can be fixed in the carrier. The transparent holder with the wafer may be detachable from the carrier so that it can be easily inserted or removed from the carrier.

As exemplarily depicted in FIG. 1 *b*, the grid-like structure may comprise support members 114, wherein in the top view of FIG. 1 *b*, an upper side of the grid-like structure is visible only. In embodiments, the mesh size of the grid structure should be chosen to be large enough so that, in the testing position, the substrate 112 with the fluidic components 115 will be accessible from opposite sides by the first and the second adapter elements 122, 124 which may extend through the grid mesh.

Figure 1B:
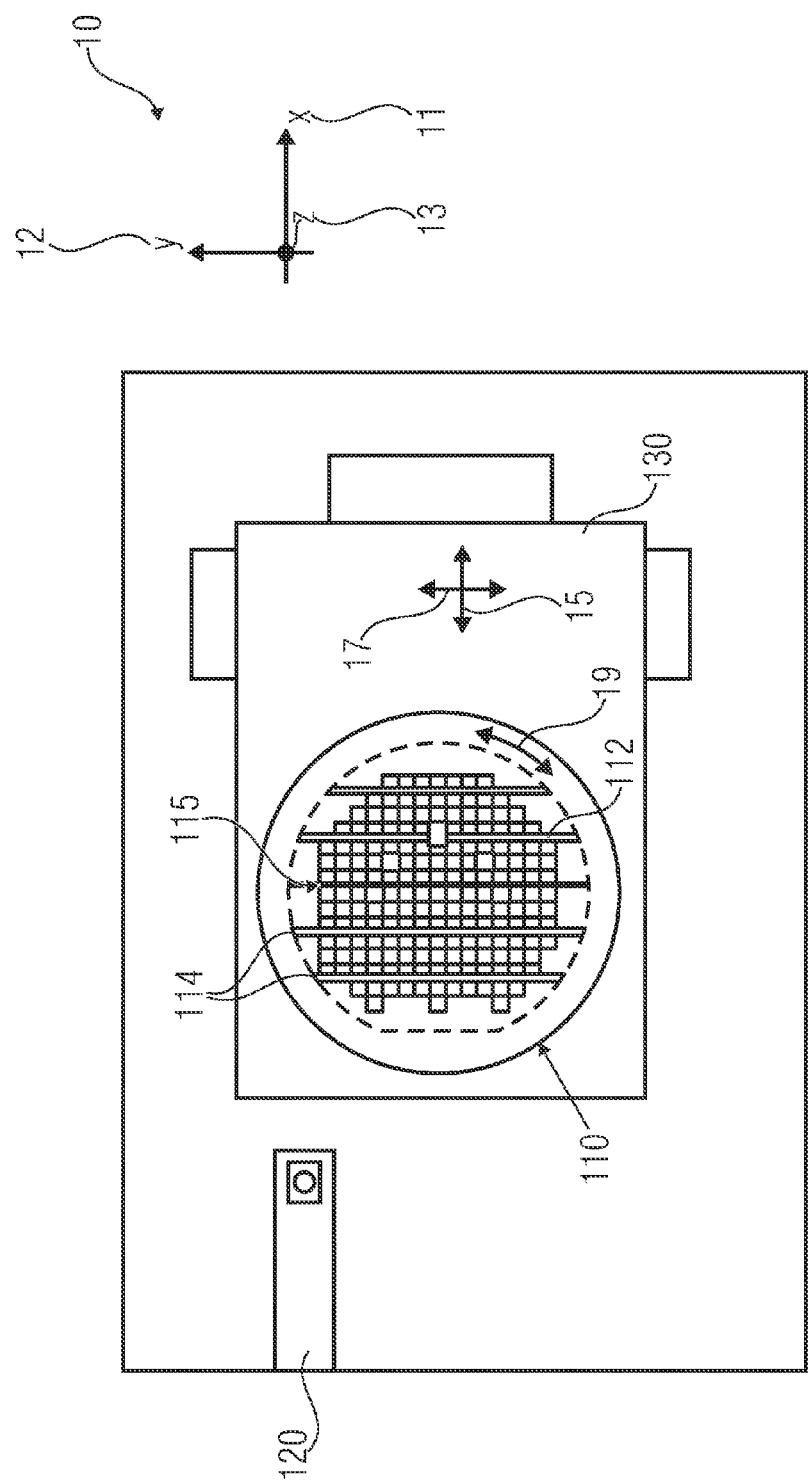

Referring to FIG. 1*b*, the displacement device or x,y-table 130 may be configured to displace the substrate 112 in the x,y-plane along a direction 15 parallel to the x-axis 11 or along a direction 17 parallel to the y-axis 12 of the coordinate system 10. Simultaneously, the carrier device 110 which is rotatable mounted to the displacement device 130 may be configured to hold and rotate the substrate 112 with the fluidic components 115 with respect to a rotational axis parallel to the z-axis 13 of the coordinate system 10. In this way, it is possible to controllably bring the substrate into the testing position. In the testing position, a respective fluidic component of the plurality 115 of fluid components is readily connectable to the first and the second adapter elements 122, 124 of the connecting device 120, as described with regard to the embodiment of FIG. 1*a*.

FIG. 1*c* shows a schematic perspective view of the embodiment of the test station 100 in accordance with FIG. 1*a*. In the perspective view of FIG. 1*c*, the carrier device 110 rotatable mounted to the displacement device 130 and the connecting device 120 with the first and the second adapter elements 122, 124 are shown. The first and the second adapter elements 122, 124 of the connecting device 120 shown in FIG. 1*c* may be arranged along a central linear axis 121 parallel to the z-axis 13. As exemplarily depicted in FIG. 1*c*, the plurality 115 of fluidic components may be arranged on a substrate 112 which is attached to the rotatable mounted carrier device 110. As described correspondingly in the top view of FIG. 1*b*, the carrier device 130 may be configured to displace the substrate 112 along a direction 15 parallel to the x-axis 11 or along a direction 17 parallel to the y-axis 12 of the coordinate system 10. In addition, the first and the second adapter elements 122, 124 may be configured to be displaced towards each other along the linear axis 121 parallel to the z-axis 13. Thus, the displacement device 130 is configured to displace the substrate 112 and the connecting device 120 relative to each other, so as to bring the substrate 112 into the testing position 105 in a flexible and controlled way.

According to a further embodiment, the test station 100 exemplarily shown in the different views of FIGS. 1*a* to 1*c* may be implemented for testing a plurality 115 of micro pumps (i.e. fluidic components) arranged on a substrate 112, wherein each of the micro pumps may comprise a connecting port. In this embodiment, the test station 100 may comprise a carrier device 110 for holding the substrate 112 with the micro pumps, a connecting device 120 for connecting the connecting port of at least one of the micro pumps located in a testing position 105 to a first adapter element 122 of the connecting device 120, and a displacement device 130 configured to displace the substrate 112 and the connecting device 120 relative to each other and to bring the substrate 112 into the testing position 105.

Referring to the embodiments of FIGS. 1*a* to 1*c*, a method for testing a plurality 115 of fluidic components arranged on a substrate 112, each of the fluidic components comprising a fluidic port, may comprise the following steps. First, the substrate 112 with the fluidic components may be held. Then, the substrate 112 may be brought into a testing position 105. Finally, in the testing position 105, the fluidic port of the at least one of the fluidic components may be fluidically connected to a first adapter element 122.

According to further embodiments, the method may further comprise measuring a fluidic characteristic of the fluidic component to be tested.

Yet according to further embodiments, the method may further comprise the following steps. First, a second adapter element 124 may be arranged in an opposing position to the first adapter element 122 with respect to the substrate 112 in the testing position 105. Then, the first adapter element 122 and the second adapter element 124 may be displaced towards each other. Finally, the first adapter element 122 and the second adapter element 124 may be brought into contact with at least one of the fluidic components from opposite sides.

According to a further embodiment of the present invention, a method for testing a plurality 115 of micro pumps arranged on a substrate 112, each of the micro pumps comprising a connecting port, may comprise the following steps. First, the substrate 112 with the micro pumps may be held. Then, the substrate 112 may be brought into a testing position 105. Finally, in the testing position 105, the connecting port of at least one of the micro pumps may be connected to a first adapter element 122.

Figure 2A:
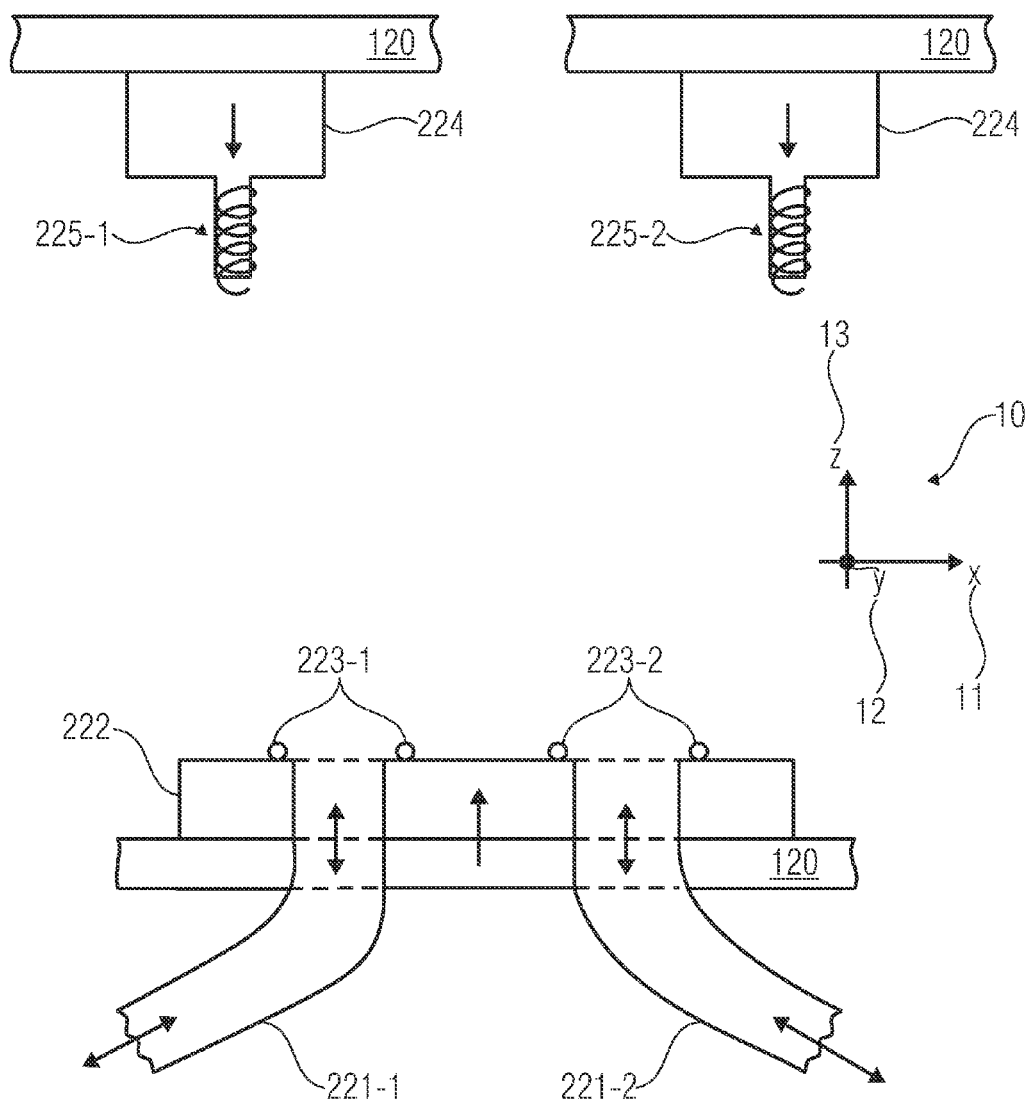
FIG. 2a shows a schematic cross-sectional view of two opposing adapter elements of a connecting device configured to be brought into contact with an fluidic component from opposite sides according to an embodiment of the present invention.
Figure 2B:
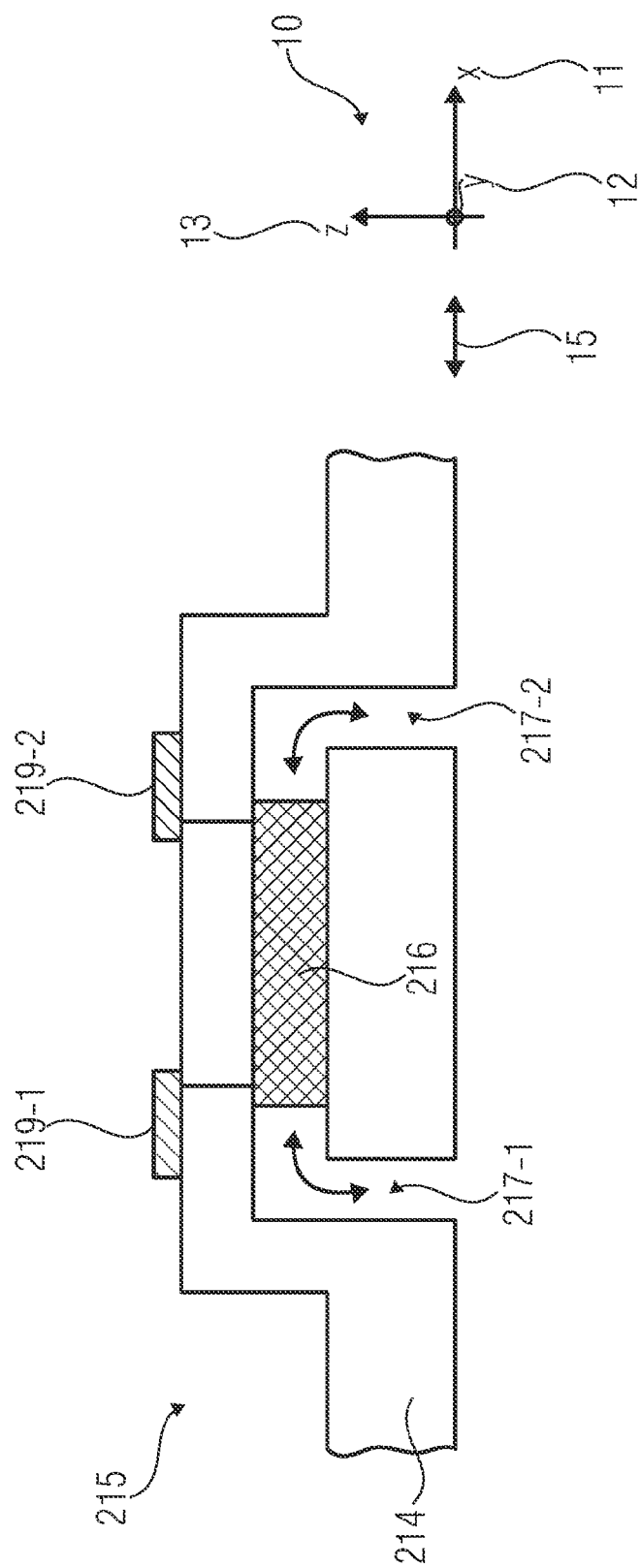

FIG. 2*a* shows a schematic cross-sectional view of two opposing adapter elements 222, 224 of a connecting device 120 configured to be brought into contact with an fluidic component 215 (see, e.g., FIG. 2*b*) from opposite sides according to an embodiment of the present invention. Referring to FIG. 2*b*, the fluidic component 215 may, for example, be a micro pump having a pump body 214 formed on or in a substrate (e.g. substrate 112). The fluidic component 215 or micro pump may comprise two electrical connecting ports 219-1, 219-2 arranged on top of the pump body 214. The two electrical connecting ports 219-1, 219-2 may be electrically connected to corresponding actuating elements for activating or driving a pumping cycle in a pump element or pump chamber 216 of the fluidic component or micro pump 215. In particular, the pump arrangement may be activated by electrically contacting the electrical connecting ports with electrical contact elements. The pump chamber 216 which is formed inside the pump body 214 of the fluidic component 215 may be fluidically connected to a first fluidic port 217-1 and a second fluidic port 217-2. As exemplarily depicted in FIG. 2b, the first and the second fluidic ports 217-1, 217-2 may be formed in the pump body 214 of the fluidic component 215. Here, the first and the second fluidic ports 217-1, 217-2 may represent fluid inlets or fluid outlets for providing a fluid flow through the fluidic component 215.

In the cross-sectional view of FIG. 2a, the two opposing adapter elements 222, 224 of the connecting device 120 may be configured to be displaced towards each other along a linear axis parallel to the z-axis 13. The first and the second adapter elements 222, 224 of FIG. 2a may correspond to the first and the second adapter elements 122, 124 of FIG. 1a. In particular, the first adapter element 222 of the connecting device 120 may comprise two fluidic contact elements 223-1, 223-2, while the second adapter element 224 of the connecting device 120 may comprise two electrical contact elements 225-1, 225-2 for electrically contacting the first and the second electrical connecting ports 219-1, 219-2 of the fluidic component 215 shown in FIG. 2b. For example, the first adapter element 222 may comprise a stamp-like block having two fluidic lines 221-1, 221-2 formed therein. In addition, the fluidic contact elements 223-1, 223-2 of the first adapter element 222 may be configured as sealing rings or square-like sealing lips attached to the upper end of the stamp-like block surrounding the outer perimeters of the fluidic lines 221-1, 221-2, respectively. Moreover, the two electrical contact elements 225-1, 225-2 of the second adapter element 224 of the connecting device 120 may each be configured as a spring or flexible metal cable contact element.

In embodiments, the fluidic component 215 may comprise two fluidic ports 217-1, 217-2 for providing a fluid inlet and a fluid outlet which can both be sealed or surrounded by respective fluidic contact elements of the first adapter element.

Referring to FIGS. 2a and b, the fluidic component 215 or micro pump may be displaced along a direction 15 parallel to the x-axis 11, so that the fluidic component 215 or micro pump of FIG. 2b will be brought between the first and the second adapter elements 222, 224 of FIG. 2a. Then, as shown in FIG. 2a, the first adapter element 222 comprising the fluidic contact elements 223-1, 223-2 may be moved upwards along the z-direction (i.e. towards the fluidic component 215 from below), so that the first and the second fluidic ports 217-1, 217-2 of the fluidic component 215 will be fluidically connected to the fluidic lines 223-1, 223-2 of the first adapter element 222. Furthermore, as shown in FIG. 2a, the second adapter element 224 comprising the two electrical contact elements 225-1, 225-2 may be displaced downwards along the z-axis 13 (i.e. towards the fluidic component 215 from above) and brought into contact with the first and the second electrical connecting ports 219-1, 219-2 of the fluidic component 215.

According to embodiments, one of the two fluidic lines 221-1, 221-2 may serve as a fluid inlet, while the other fluidic line may serve as a fluid outlet. For example, the fluidic line 221-1 may serve as the fluid inlet and the fluidic line 221-2 may serve as the fluid outlet. Alternatively, the fluidic line 221-1 may serve as the fluid outlet and the fluidic line 221-2 may serve as the fluid inlet. The two cases may correspond to two opposing flow directions through the pump chamber 216 of the fluidic component 215.

According to further embodiments, one of the two fluidic lines 221-1, 221-2 may be terminated for defining a closed (predefined) volume, while the other fluidic line may be open and serve as a fluid inlet or as a fluid outlet.

Therefore, by providing the above configurations for the two fluidic lines 221-1, 221-2, different fluidic tests can be performed. In case that one fluidic line serves as the fluidic inlet and the other fluidic line serves as the fluidic outlet, a flow measurement can be performed for a fluid flow in either direction through the pump chamber 216 of the fluidic component 215. In case that one fluidic line defines a predefined volume and the other fluidic line serves as a fluid inlet or as a fluid outlet, a pressure test or a suction test can be performed by compressing or decompressing a fluidic medium of the predefined volume, respectively.

Figure 3:
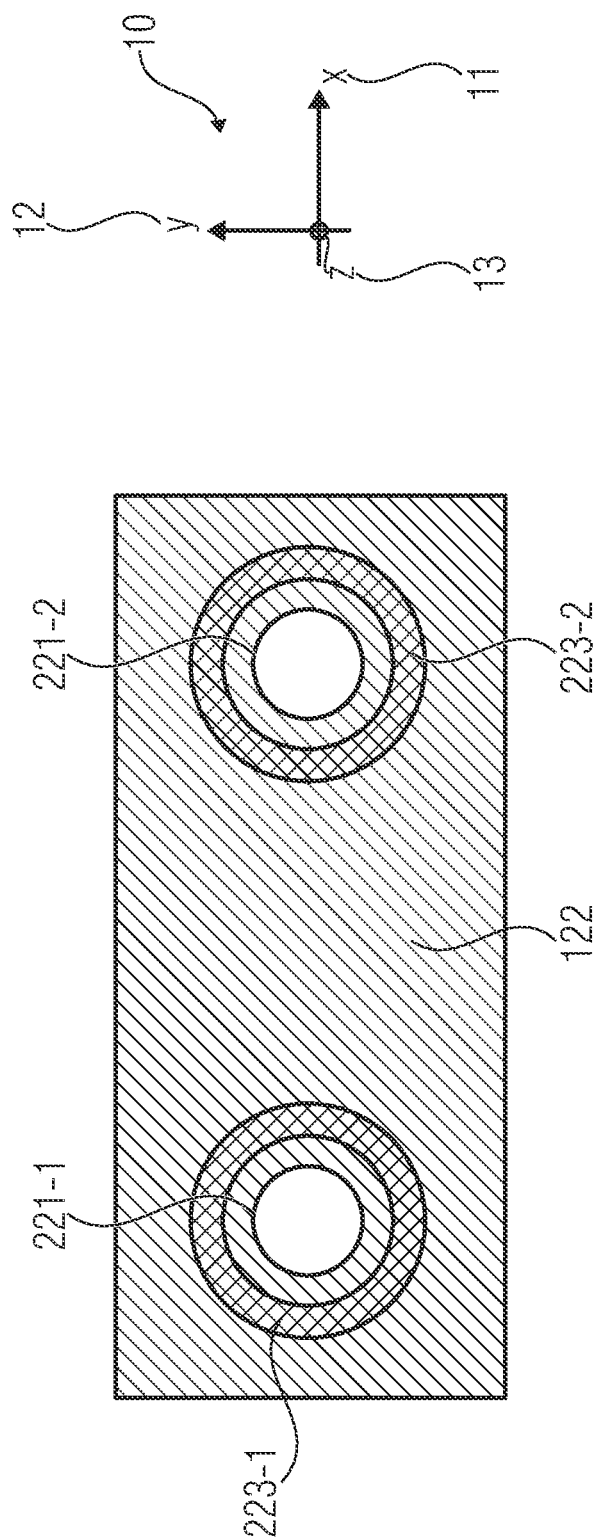
FIG. 3 shows a schematic top view of a first adapter element with opening regions of fluidic lines surrounded by sealing rings according to a further embodiment of the present invention.

FIG. 3 shows a schematic top view of a first adapter element 122 with opening regions of the fluidic lines 221-1, 221-2 surrounded by the fluidic contact elements 223-1, 223-2 according to a further embodiment of the present invention. The fluidic contact elements 223-1, 223-2 are configured, for example, as sealing rings for surrounding the outer perimeters of the fluidic lines 221-1, 221-2. In embodiments, the fluidic contact elements 223-1, 223-2 of the first adapter element 122 which are configured as sealing rings may be brought into contact with the substrate 112 of the pump body 214, such that the fluidic ports 217-1, 217-2 of the fluidic component 215 will be surrounded by the fluidic contact element 223-1, 223-2 of the first adapter element 122. In particular, the first adapter element 122 comprising the fluidic contact elements 223-1, 223-2 may be displaced by the connecting device 120 towards the fluidic component 215 along a direction parallel to the z-axis 13 of the coordinate system 10. This allows to fluidically connect the fluidic ports 217-1, 217-2 of the fluidic component with the first adapter element 122 or the fluidic lines 221-1, 221-2 formed therein.

In embodiments, each of the fluidic ports 217-1, 217-2 of the fluidic component may be fluidically connected to the first adapter element by using a respective fluidic contact element being shaped as an O-ring (see, e.g. FIG. 3). Alternatively, the respective fluidic contact element may have a square-like shape. In further embodiments, the two fluidic contact elements for the two fluidic ports 217-1, 217-2 may together have a shape of a double O-ring with two neighboring individual O-rings. Alternatively, the two fluid contact elements may together have a shape of a double square with two neighboring square-like contact elements or a flat sealing with two or more openings which match to the form and the number of openings of the fluidic device.

FIGS. 4a to 4e show schematic illustrations of two opposing adapter elements of a connecting device which are displaceable towards each other with different configurations of a first adapter element 322-1, 322-2, 322-3, 322-4, 322-5 and a second adapter element 324-1, 324-2, 324-3, 324-4, 324-5 according to different embodiments of the present invention. In FIGS. 4a to 4e, different embodiments of fluidic components 315-1, 315-2, 315-3, 315-4, 315-5 that can be arranged on a substrate are shown.

Figure 4A:
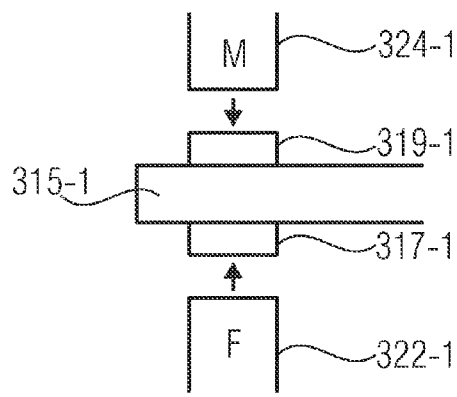
FIG. 4a shows a schematic illustration of two opposing adapter elements of a connecting device which are displaceable towards each other with a first adapter element comprising a fluidic contact element and a second adapter element comprising a mechanical contact element according to a further embodiment of the present invention.

In the configuration of FIG. 4a, the fluidic component 315-1 may comprise a fluidic port 317-1 on a first side of the fluidic component 315-1 and an electrical connecting port 319-1 on a second side of the fluidic component 315-1. The two opposing adapter elements in the configuration of FIG. 4a are configured to be brought into contact with the fluidic component 315-1 from opposite sides as indicated by the arrows pointing towards the fluidic component 315-1. As exemplarily depicted in the configuration of FIG. 4a, the first adapter element 322-1 may comprise a fluidic contact element, while the second adapter element 324-1 may comprise a mechanical contact element. In particular, the first adapter element 322-1 comprising the fluidic contact element may be configured to fluidically connect the fluidic port 317-1 of the fluidic component 315-1 from the first side of the fluidic component 315-1. In addition, the second adapter element 324-1 comprising the mechanical contact element may be configured to mechanically contact the electrical connecting port 319-1 of the fluidic component 315-1 from the second side of the fluidic component 315-1.

According to the configuration of FIG. 4a, the mechanical contact element of the second adapter element 324-1 is, for example, configured as a stamp-like block to induce an opposing pressure against the fluidic component 315-1, so that the fluidic component 315-1 can be fixed more reliably between the first and the second adapter elements 322-1, 324-1.

Figure 4B:
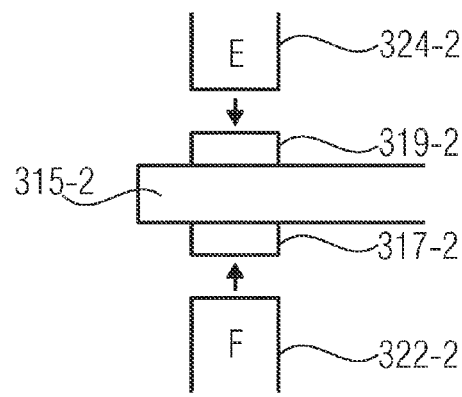
FIG. 4b shows a schematic illustration of two opposing adapter elements of a connecting device which are displaceable towards each other with a first adapter element comprising a fluidic contact element and a second adapter element comprising an electrical contact element according to a further embodiment of the present invention.

In the configuration of FIG. 4b, the fluidic component 315-2 may comprise a fluidic port 317-2 on a first side of the fluidic component 315-2 and an electrical connecting port 319-2 on a second side of the fluidic component 315-2. The two opposing adapter elements in the configuration of FIG. 4b are configured to be brought into contact with the fluidic component 315-2 from opposite sides as indicated by the arrows pointing towards the fluidic component 315-2. As exemplarily depicted in the configuration of FIG. 4b, the first adapter element 322-2 may comprise a fluidic contact element, while the second adapter element 324-2 may comprise an electrical contact element. In particular, the first adapter element 322-2 comprising the fluidic contact element may be configured to fluidically connect the fluidic port 317-2 of the fluidic component 315-2 from the first side of the fluidic component 315-2. In addition, the second adapter element 324-2 comprising the electrical contact element may be configured to electrically contact the electrical connecting port 319-2 of the fluidic component 315-2 from the second side of the fluidic component 315-2.

According to the configuration of FIG. 4b, the fluidic component 315-2 can be fluidically connected from one side and electrically contacted from an opposing side, so that on the one hand, the fluidic medium will be provided for the fluidic component 315-2 and on the other hand, a pumping cycle of the fluidic component 315-2 can be activated or electrically driven.

Figure 4C:
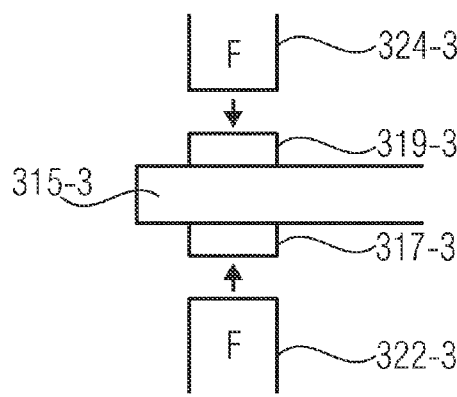
FIG. 4c shows a schematic illustration of two opposing adapter elements of a connecting device which are displaceable towards each other with each of the adapter elements comprising a fluidic contact element according to a further embodiment of the present invention.

In the configuration of FIG. 4c, the fluidic component 315-3 may comprise a fluidic port 317-3 on a first side of the fluidic component 315-3 and a fluidic port 319-3 on a second side of the fluidic component 315-3. The two opposing adapter elements in the configuration of FIG. 4c are configured to be brought into contact with the fluidic component 315-3 from opposing sides as indicated by the arrows pointing towards the fluidic component 315-3. As exemplarily depicted in the configuration of FIG. 4c, the first adapter element 322-3 may comprise a fluidic contact element and the second adapter element 324-3 may comprise a fluidic contact element. In particular, the first adapter element 322-3 comprising the fluidic contact element may be configured to fluidically connect the fluidic port 317-3 of the fluidic component 315-3 from the first side of the fluidic component 315-3. In addition, the second adapter element 324-3 comprising the fluidic contact element may be configured to fluidically contact the fluidic port 319-3 of the fluidic component 315-3 from the second side of the fluidic component 315-3.

According to the configuration of FIG. 4c, the fluidic component 315-3 can be fluidically connected from opposite sides, wherein the first and the second adapter elements 322-3, 324-3 are implemented to provide a fluid inlet or a fluid outlet for inputting or outputting a fluidic medium for the fluidic component 315-3.

Figure 4D:
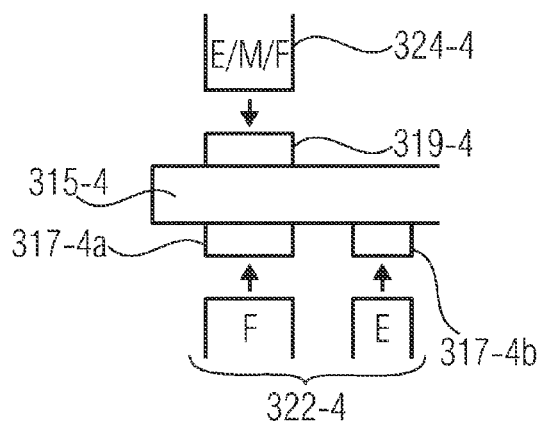
FIG. 4d shows a schematic illustration of two opposing adapter elements of a connecting device which are displaceable towards each other with the first adapter element comprising a fluidic contact element and an electrical contact element and a second adapter element comprising an electrical, mechanical or fluidic contact element according to a further embodiment of the present invention.

In the configuration of FIG. 4d, the fluidic component 315-4 may comprise a fluidic port 317-4a and an electrical connecting port 317-4b on a first side of the fluidic component 315-4 and a fluidic port or an electrical connecting port 319-4 on a second side of the fluidic component 315-4. The two opposing adapter elements in the configuration of FIG. 4d are configured to be brought into contact with the fluidic component 315-4 from opposite sides as indicated by the arrows pointing towards the fluidic component 315-4. As exemplarily depicted in the configuration of FIG. 4d, the first adapter element 322-4 may comprise a fluidic contact element and an electrical contact element, while the second adapter element 324-4 may comprise an electrical contact element, a mechanical contact element or a fluidic contact element. In particular, the first adapter element 322-4 comprising the fluidic contact element and the electrical contact element may be configured to fluidically connect the fluid port 317-4a and to electrically contact the electrical connecting port 317-4b of the fluidic component 315-4 from the first side of the fluidic component 315-4. In addition, the second adapter element 324-4 comprising the electrical contact element, mechanical contact element or fluidic contact element may be configured to electrically contact, to mechanically contact or to fluidically connect the fluidic port or the electrical connecting port 319-4 of the fluidic component 315-4 from the second side of the fluidic component 315-4.

According to the configuration of FIG. 4d, the fluidic component 315-4 can be fluidically connected and electrically contacted from one side of the fluidic component 315-4, while the fluidic component 315-4 can be electrically contacted, mechanically contacted or fluidically connected from the opposite side of the fluidic component 315-4.

Figure 4E:
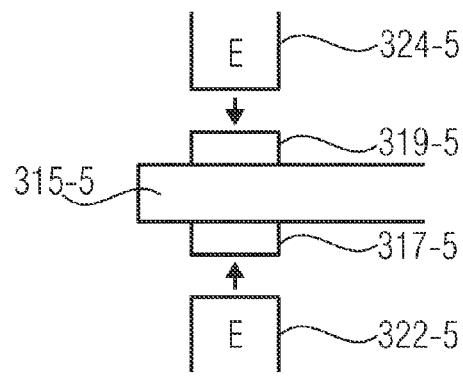
FIG. 4e shows a schematic illustration of two opposing adapter elements of a connecting device which are displaceable towards each other with each of the adapter elements comprising an electrical contact element according to a further embodiment of the present invention.

In the configuration of FIG. 4e, the fluidic component 315-5 may comprise a first electrical connecting port 317-5 on a first side of the fluidic component 315-5 and a second electrical connecting port 319-5 on a second side of the fluidic component 315-5. The two opposing adapter elements in the configuration of FIG. 4e are configured to be brought into contact with the fluidic component 315-5 from opposite sides as indicated by the arrows pointing towards the fluidic component 315-5. As exemplarily depicted in the configuration of FIG. 4e, the first adapter element 322-5 may comprise an electrical contact element and the second adapter element 324-5 may comprise an electrical contact element. In particular, the first adapter element 322-5 comprising the electrical contact element may be configured to electrically contact the first electrical connecting port 317-5 of the fluidic component 315-5 from the first side of the fluidic component 315-5. In addition, the second adapter element 324-5 comprising the electrical contact element may be configured to electrically contact the second electrical connecting port 319-5 of the fluidic component 315-5 from the second side of the fluidic component 315-5.

According to the configuration of FIG. 4e, the fluidic component 315-5 can be electrically contacted from two opposite sides so as to provide an electrical current on both sides of the fluidic component 315-5.

In the different configurations of FIGS. 4a to 4e, an electrical contact element is denoted by 'E', the mechanical contact element is denoted by 'M' and a fluidic contact element is denoted by 'F'. Moreover, the first adapter elements 322-1, 322-2, 322-3, 322-4, 322-5 of FIGS. 4a to 4e may correspond to the first adapter element 122 of the connecting device 120 of FIG. 1a, while the second adapter elements 324-1, 324-2, 324-3, 324-4, 324-5 of FIGS. 4a to 4e may correspond to the second adapter element 124 of the connecting device 120 of FIG. 1a.

Referring to the different embodiments of FIGS. 4a to 4e, the first adapter elements 322-1, 322-2, 322-3, 322-4, 322-5 may comprise a contact element selected from a group consisting of a fluidic contact element, an electrical contact element and a mechanical contact element.

Furthermore, the second adapter elements 324-1, 324-2, 324-3, 324-4, 324-5 may comprise a contact element selected from a group consisting of a fluidic contact element, an electrical contact element and a mechanical contact element.

In embodiments, the first adapter elements and the second adapter elements may each comprise a contact element selected from a group consisting of a fluidic contact element, an electrical contact element and a mechanical contact element, wherein the first adapter elements and the second adapter elements are of different types (see, e.g. FIGS. 4a and 4b). In particular, the fluidic component may be fluidically connected by a fluidic contact element and mechanically contacted by a mechanical contact element from opposite sides as shown in FIG. 4a or fluidically connected by a fluidic contact element and electrically contacted by an electrical contact element from opposite sides as shown in FIG. 4b.

Referring to the configuration of FIG. 4d, the first adapter element 322-4 may comprise a fluidic contact element and an electrical contact element. Thus, the fluidic component can be fluidically connected by a fluidic contact element and electrically contacted by an electrical contact element from the same side of the fluidic component.

Referring to the configuration of FIG. 4a-e, the fluidic contact element and/or the connecting device can be spring suspended in order to limit the mechanical load or to avoid a mechanical overload or overstressing of the fluidic component(s) to be tested and/or of the substrate having arranged thereon the fluidic component(s).

Figure 5A:
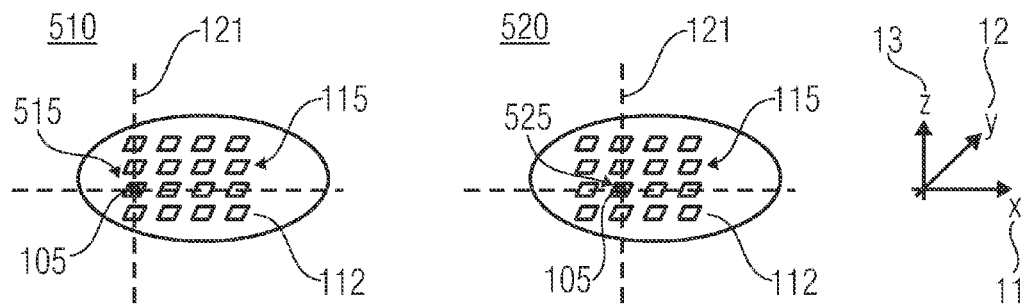
FIGS. 5a-5c show different configurations for fluidically connecting fluidic ports of different fluidic components or different groups of fluidic components for two different phases.
Figure 5B:
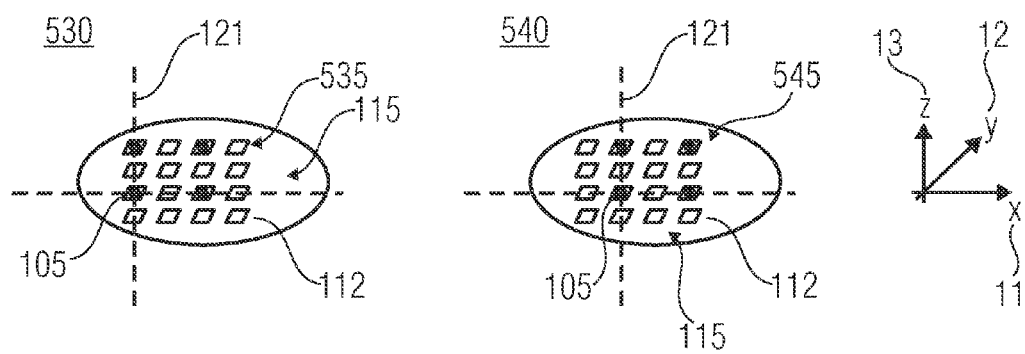
Figure 5C:
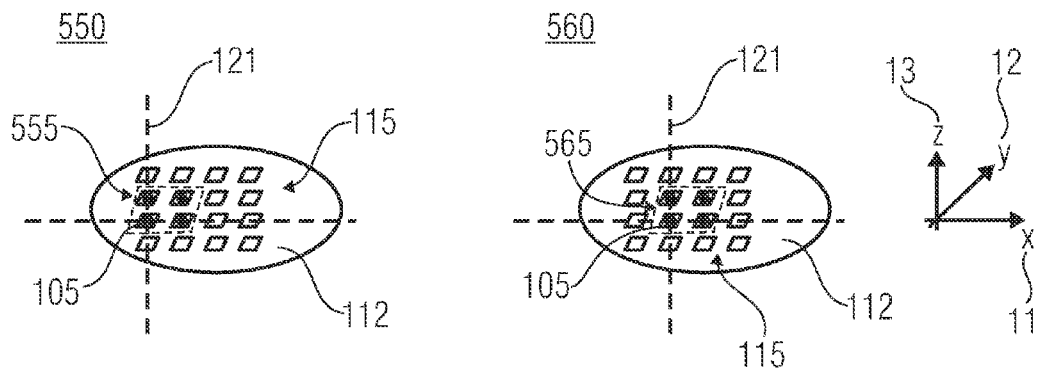

FIGS. 5a to 5c show different configurations for fluidically connecting fluidic ports of different fluidic components or different groups of fluidic components for two different phases. The two different phases in the configurations of FIGS. 5a to 5c essentially correspond to two different arrangements or alignments of the substrate 112 carrying the fluidic components 115 with respect to the linear axis 121 or the testing position 105. Here, the different arrangements of the substrate 112 may be obtained from a displacement parallel to the x-axis 11 by the use of the displacement device 130.

According to the configuration of FIG. 5a, the displacement device 130 may be configured to bring, in a first phase 510, a first fluidic component 515 into the testing position 105, so that, in the first phase 510, the fluidic port of the first fluidic component 515 will be fluidically connected to the first adapter element 122. In addition, the displacement device 130 may be configured to bring, in a second phase 520, a second fluidic component 525 into the testing position 105, so that, in the second phase 520, the fluidic port of the second fluidic component 525 will be fluidically connected to the first adapter element 122.

According to the configuration of FIG. 5b, the displacement device 130 may be configured to bring, in a first phase 530, a first group 535 of fluidic components into the testing position 105, so that, in the first phase 530, fluidic ports of the first group 535 of fluidic e components will be fluidically connected to the first adapter element 122. In addition, the displacement device 130 may be configured to bring, in a second phase 540, the second group 545 of fluidic components into the testing position 105, so that, in the second phase 540, fluidic ports of the second group 545 of fluidic components will be fluidically connected to the first adapter element 122.

According to the configuration of FIG. 5c, the displacement device 130 may be configured to bring, in a first phase 550, a first group 555 of neighboring fluidic components into the testing position 105, so that, in the first phase 550, fluidic ports of the first group 555 of neighboring fluidic components will be fluidically connected to the first adapter element 122. In addition, the displacement device 130 may be configured to bring, in a second phase 560, a second group 565 of neighboring fluidic components into the testing position 105, so that, in the second phase 560, fluid ports of the second group 565 of neighboring fluidic components will be fluidically connected to the first adapter element 122.

Specific to the configuration of FIG. 5c is that the first adapter element 122 may be configured to simultaneously fluidically contact a group 555; 565 of neighboring fluidic components (i.e., in the first phase 550, simultaneously fluidically connecting the group 555 and in the second phase 560, simultaneously fluidically connecting the group 565).

Figure 6:
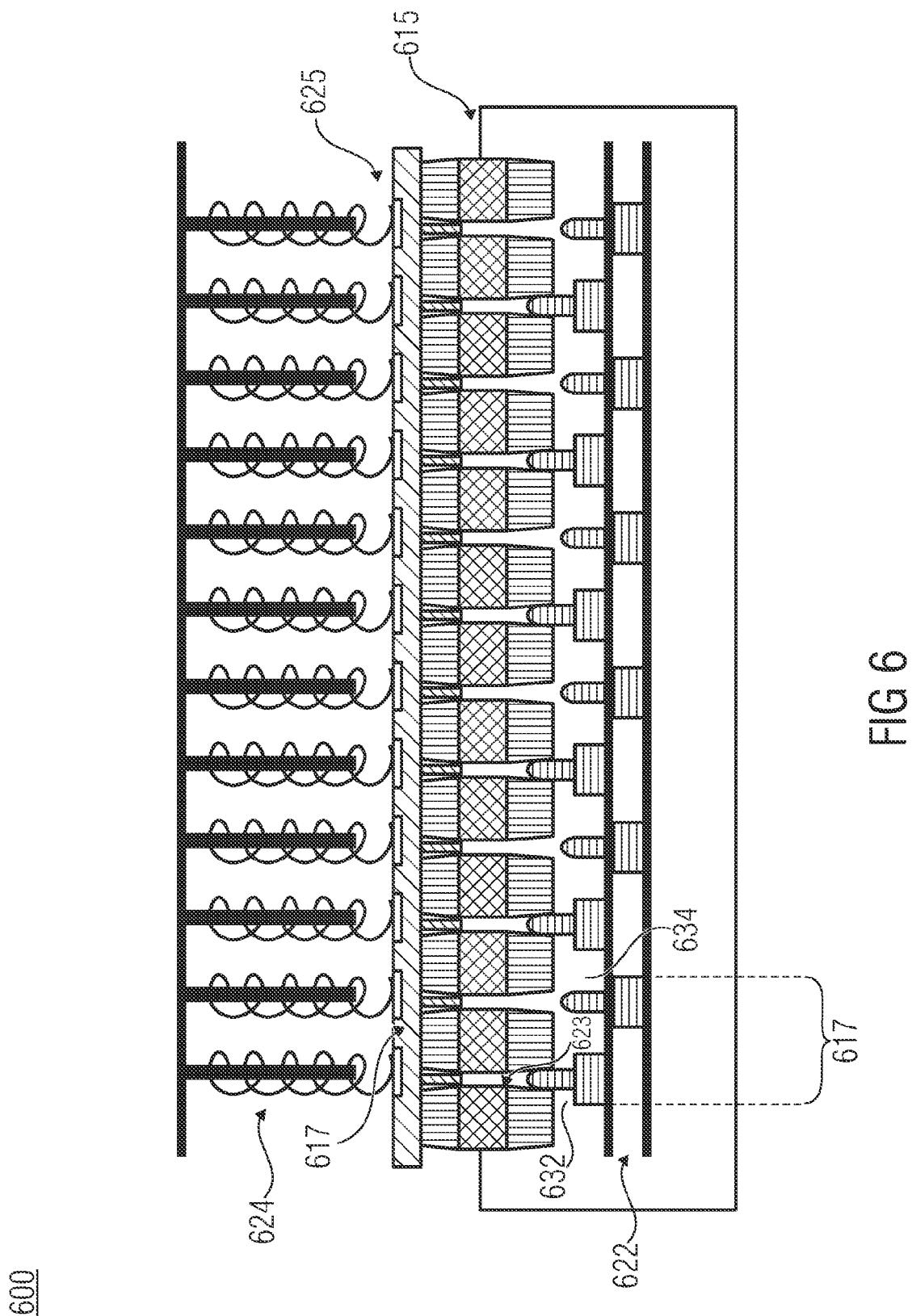
FIG. 6 shows a schematic illustration of an arrangement of two opposing adapter elements of a connecting device for testing a group of micro pumps according to a further embodiment of the present invention.

FIG. 6 shows a schematic illustration of an arrangement 600 of two opposing adapter elements 622, 624 of a connecting device for testing a group 615 of active or passive fluidic components, e.g. micro pumps, micro valves, etc. according to a further embodiment of the present invention. In the arrangement 600 of FIG. 6, a first adapter element 622 may be fluidically connected to fluidic ports 623 of the group 615 of micro pumps, while a second adapter element 624 may be electrically contacted to electrical connecting ports 625 of the group 615 of micro pumps. Here, the first and the second adapter element 622, 624 and the group 615 of micro pumps in the embodiment of FIG. 6 may correspond to the first and the second adapter elements 122, 124 and the plurality 115 of fluidic components in the embodiment of FIG. 1a. The group 615 of micro pumps may comprise an individual micro pump 617 having two fluidic ports for providing a fluid inlet and fluid outlet and two electrical connecting ports for driving a pumping cycle of the individual micro pump 617. In the embodiment of FIG. 6, the first adapter element 622 may comprise a first fluidic contact element 632 for providing a fluidic connection to a fluid inlet of the individual micro pump 617 and a second fluidic contact element 634 for providing a fluidic connection to a fluid outlet of the individual micro pump 617. Specifically, the first and the second fluidic contact elements 632, 634 are, for example, used to perform a suction test or a pressure test. Here, the first fluidic contact element 632 may be provided for the fluidic inlet, while the second fluidic contact element 634 may be provided for the fluidic outlet. According to the embodiment of FIG. 6, each of the group 615 of micro pumps may be individually characterized by such a suction test or pressure test.

Figure 7:
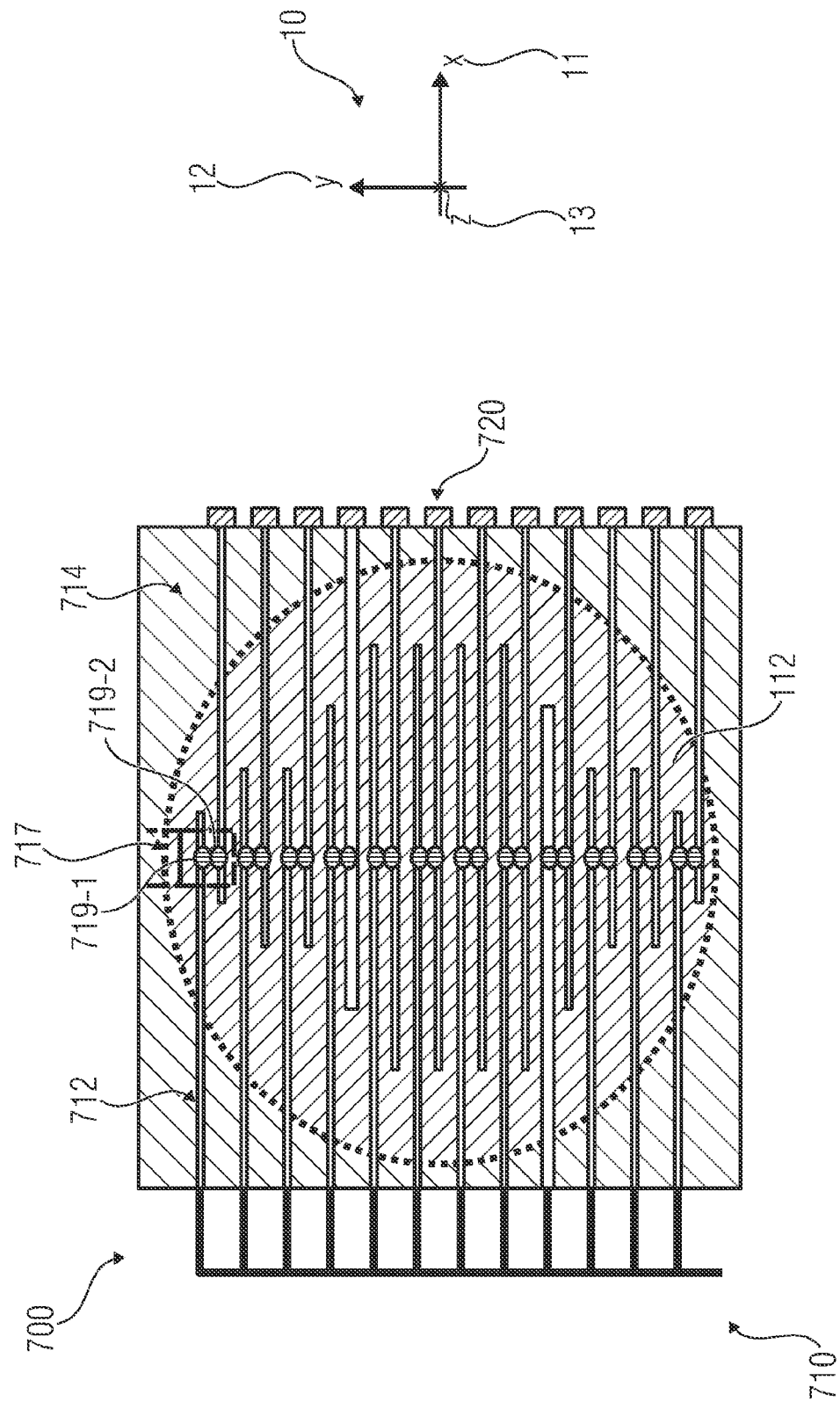
FIG. 7 shows a schematic illustration of a first adapter element of a connecting device for testing a group of micro pumps according to a further embodiment of the present invention.

FIG. 7 shows a schematic illustration of a first adapter element 700 of a connecting device for testing a group of micro pumps according to a further embodiment of the present invention. In the schematic illustration of FIG. 7, the substrate 112 including the fluidic (MEMS) components or micro pumps, micro valves . . . , is shown in a bottom view. In this bottom view, the substrate 112 essentially extends in an x,y-plane defined by the x-axis 11 and the y-axis 12 of the coordinate system 10. The z-axis 13 of the coordinate system 10 is essentially perpendicular to this x, y-plane. As exemplarily depicted in FIG. 7, the first adapter element 700 may comprise an air intake structure 710 and a plurality 720 of pressure sensors. In particular, the air intake structure 710 may be fluidically connected to corresponding first fluidic ports 719-1 of respective MEMS components via a first plurality 712 of fluidic lines, while the plurality 720 of pressure sensors may be fluidically connected to corresponding second fluidic ports of the respective fluidic components via a second plurality 714 of fluidic lines. The first and the second fluidic ports 719-1, 719-2 that can be fluidically connected to the air intake structure 710 and the plurality 720 of pressure sensors may together constitute fluidic ports 717 of individual fluidic components to be tested.

In embodiments, the first and the second plurality 712, 714 of fluidic lines of the first adapter element 700 may be directed or extend parallel to the z-axis 13 and may be implemented to be brought into contact with the fluidic components in a direction parallel to the z-axis 13.

By providing the first adapter element 700 with the air intake structure 710 and the plurality 720 of pressure sensors for fluidically connecting the fluidic ports 717 of the fluidic components to be tested, various fluidic tests of the fluidic components can be performed, such as micro pump tests, micro valve tests, . . . on wafer level.

For example, during such a micro pump test on wafer level, a measurement method can be employed, wherein micro pumps are contacted fluidically (e.g. individually or in parallel). In particular, at the outlet of a micro pump to be tested, a pressure sensor may be adapted. Here, a defined volume lies between the micro pump and the pressure sensor. According to embodiments, the micro pump (on the wafer or substrate) pumps this volume. This, in turn, causes a defined pressure increase up to a saturation pressure. After turning off the micro pump, the leakage rates of the pump valves can be inferred by means of a slow decrease of the excess pressure. By analyzing, for example, a transient measured pressure signal such as by a sensor device described with regard to the previous embodiments, different quality parameters of the micro pump can be measured (e.g., compression ratio, displaced volume, delivery rate depending on the back pressure, or leakage rate).

In embodiments described above with regard to FIGS. 6 and 7, eight pumps can be measured in parallel. However, the volumes of the other pumps in a row may influence the measurement result. Therefore, it may be a further option to install an individual sensor for each pump. In this way, the pressure volumes could also be unified.

Figure 8:
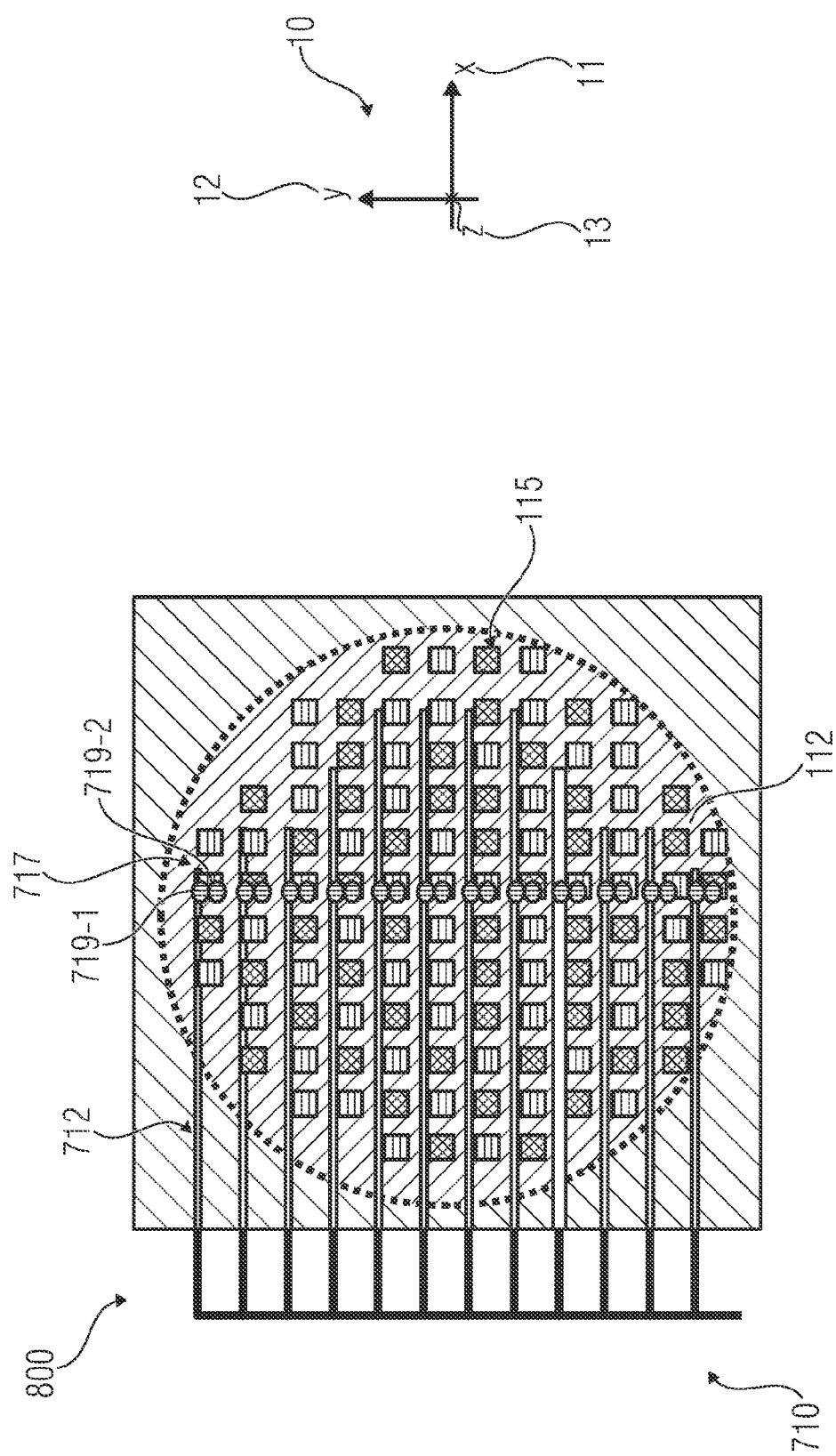
FIG. 8 shows a schematic illustration of a first adapter element of a connecting device for testing a group of micro pumps according to a further embodiment of the present invention.

FIG. 8 shows a schematic illustration of a first adapter element 800 of a connecting device for testing a group of micro pumps according to a further embodiment of the present invention. Referring to FIG. 8, the substrate 112 with the fluidic components 115 or group of micro pumps is shown in a bottom view, wherein the substrate 112 is essentially lying in the x,y-plane defined by the x-axis 11 and the y-axis 12 of the coordinate system 10. Here, each of the group of micro pumps may comprise a pair of fluidic ports having a first fluidic port 719-1 and a second fluidic port 719-2. As can be seen in FIG. 8, the air intake structure 710 of the first adapter element 800 may be fluidically connected to corresponding first fluidic ports 719-1 of respective fluidic components via the first plurality 712 of fluidic lines, while the second fluid ports 719-2 of the respective fluidic components may essentially be fluidically terminated. In embodiments, the first plurality 712 of fluidic lines of the first adapter element 800 may be directed or extend parallel to the z-axis 13 and may be implemented to be brought into contact with the fluidic components in a direction parallel to the z-axis 13, as previously described with regard to FIG. 7.

By using such a configuration of the first adapter element 800, some more testing methods can be performed for obtaining different fluidic characteristics of the fluidic components or group of micro pumps.

In embodiments, several different tests can be integrated for gases and liquids, for example, for wafers of 4 to 12" (450 mm) or multiple-shape components of corresponding size. Such tests may include fluidic tests, electrical tests or optical tests. In particular, fluidic tests may comprise a detection of flow rates with and without back pressure, a measurement of leakage rates or sticking tests. Electrical tests comprise, for example, measuring capacities of piezos, measuring impedances, characterizing membranes, examining electrical characteristics of actuators (current, resistance, etc.), or capacitive measurements such as flow measurements. Optical tests comprise, for example, a determination of the position of glued piezos, or an examination of tools (e.g., examining a sealing surface or detachable electrical contact on combustions as a result of a short circuit).

For additional measurements, depending on the requirements, different sensors or sensor devices, such as flow sensors, pressure sensors, temperature sensors, acceleration sensors, optical sensors (e.g., for a deviation measurement by a laser) or chemical sensors (e.g., pH O2, H2, . . . ), force sensors, etc., can be integrated directly into the stamps (e.g. the first or second adapter element of the connecting device of the test station) or measurement devices. For example, the measurement devices necessitated, such as flow sensors, pressure controller, etc., can be integrated into the device or test station.

According to further embodiments, the individual test methods can be processed or performed on wafer level. For testing, for example, 200 chips on a 6" wafer one after the other, both fluidic and electrical contacting (e.g. by the fluidic and electrical contact elements) may be designed as detachable units. The arrangement of the two contact units or first and second adapter elements can, for example, be such that the contact units will be applicable for both electrically contacting from the top or fluidically connecting from the bottom of a fluidic component and also vice versa. In this case, the wafer or fluidic component to be tested may be arranged horizontally and the contact units can be arranged perpendicular to the wafer. Alternatively, a vertical (perpendicular) arrangement of the wafer or fluidic component is also possible, wherein in this case, the respective contact units or first and second adapter elements may be arranged horizontally. In one embodiment, the wafer is arranged horizontally, while the contacting is performed perpendicular to the wafer.

In embodiments, the contact units or first and second adapter elements can be arranged on linear axes, such that they will be in one level to each other, wherein the wafer or substrate is firmly clamped in a receptacle. In other embodiments, it is also possible to arrange the wafer or substrate on linear axes. Fluidic seals according to embodiments of the present invention should be resistant to fluidic media (e.g., for different oil types, hydrazine).

In further embodiments, an automatic change of the contact units, designed for different fluidic components (e.g., micro valves, micro pumps) can be integrated. On the one hand, electrical contacting or electrical contact elements consisting of a holder with, for example, a spring pin, a thin wire (e.g., a bond wire) such as applied on a piezo, and spring contacts (e.g., soft spiral springs, sheet springs) may be used. On the other hand, fluidic contacting or fluidic contact elements consisting of a holder with a receptacle for a seal designed for a fluidic arrangement of the device and a seal may be used.

According to embodiments of the present invention, the measurements (methods) can be performed by both electrically contacting and fluidically contacting, or by only fluidically connecting, or by only electrically connecting in two separate contact units, or by electrically contacting and fluidically connecting in one contact unit.

In embodiments, the wafer carrier or carrier device, which is accessible from both sides thereof, may be configured such that the wafer or substrate will be firmly clamped into the receptacle by hand (manually). In addition, the wafer carrier may comprise a semiautomatic device clamping the wafer, or an automatic wafer reception connected to a wafer transport system for automatically changing wafers (e.g., frog legs or other common changing systems) for large quantities of the same. Here, the wafer carrier is, for example, configured such that the wafer can be arranged to be rotatable by 360°.

Embodiments of the present invention provide a measurement device or a test station for characterizing fluidic components, such as micro pumps, valves, mixers, drop dispensers passively and actively driven (e.g., piezo actuated, electrostatically), in a computer controlled/automatic manner on wafer level for different fluidic media (e.g., gases and liquids having different viscosities), by one or several fluidic lines for contacting a fluidic port arranged at any wafer position (X, Y) and thereby fluidically contacting the fluidic component and, hence, providing the prerequisite that the same can be characterized fluidically.

In embodiments, the fluidic connection or first and second adapter elements are, for example, configured to be detachable or non-detachable.

In further embodiments, a parallelization of the testing method can be realized. For example, a single component examination with an x,y-table, an array examination with an x,y-table, or a full contacting of the whole wafer or substrate can be performed.

In yet further embodiments, the fluidic characterization of the fluidic component may be performed by the use of a flow sensor based, for example, on an anemometric or differential pressure principle, a pressure sensor or an optical sensor (e.g., for a mixer).

In some embodiments, there may be two detachable connections for electrically contacting and fluidically connecting the fluid component.

With regard to the wafer reception, there can be two different designs comprising, for example, a receptacle for manually inserting the wafer or substrate with a subsequent clamping, or a receptacle with is designed for an automatic insertion. Specifically, a cantilever clamping can be used. The clamping position may be horizontal or perpendicular.

In further embodiments, the positioning of the wafer or substrate and the contact elements or first and second adapter elements can be realized with linear (positioning) axes. There are, for example, two positioning options. The contact units or first and second adapter elements can be moved essentially in the z-direction, while the wafer or substrate can be moved in the x,y-level or plane. Alternatively, the stamp or first adapter element can be moved in the x,y,z-plane, while the wafer or substrate is fixed.

Embodiments of the present invention provide measurement methods including sequential processing of individual components on the wafer, flow measurements with and without back pressure, detection of leakage rates in and against flow direction, detection of pressure, opening pressure of valves (e.g. threshold pressure), signal tests by varying the control signals (e.g. square, sinus, triangle), capturing electrical characteristics (e.g. capacity, current consumption), sticking tests, characterization of micro mixers (e.g. three fluid ports per fluidic component), characterization of drop dispensers (e.g. Back Shooter or Top Shooter) and characterization of fluidic components with liquids such as by serially adding different liquids (e.g. lubricating oil for measurement, then isopropanol for cleaning and air for drying).

In summary, embodiments of the present invention provide an automatic test station adaptable to a broad spectrum of fluidic components in a modular manner, wherein this test device is in particular adapted for silicon devices on wafer level or other materials such as plastics, stainless steel, ceramics having a plurality of shapes both for gases and liquids. Testing individual components, especially not on wafer level, is also possible with specific adapters. The test station can, in particular, be used for a pre-characterization and selection of processed pump chips according to "good dies" and "bad dies".

As opposed to conventional technology, where fully automated test devices are only known for pressure sensors that characterize the membranes and their vibration behavior on wafer level, and wherein for more extensive characterizations, frequently, several measurement stations are necessitated, embodiments of the present invention provide a concept for characterizing fluidic components in a cost-effective manner, thereby realizing an automatic test device which is suitable, in particular, for the characterization of large quantities of such fluidic components.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

The above described embodiments are merely illustrative for the principles of the present invention. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

Depending on certain implementation requirements, embodiments of the invention can be implemented in hardware or in software. The implementation can be performed using a digital storage medium, for example a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may for example be stored on a machine readable carrier.

Other embodiments comprise the computer program for performing one of the methods described herein, stored on a machine readable carrier. In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitionary. A further embodiment of the inventive method is, therefore, a data stream or a sequence of signals representing the computer program for performing one of the methods described herein. The data stream or the sequence of signals may for example be configured to be transferred via a data communication connection, for example via the Internet. A further embodiment comprises a processing means, for example a computer, or a programmable logic device, configured to or adapted to perform one of the methods described herein. A further embodiment comprises a computer having installed thereon the computer program for performing one of the methods described herein. A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods may be performed by any hardware apparatus.

While this invention has been described in terms of several embodiments, there are alterations, permutations, and equivalents which will be apparent to others skilled in the art and which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. A test station for testing at least one fluidic component arranged on a substrate, each fluidic component comprising a fluidic port, the test station comprising:
   a carrier device for holding the substrate with the at least one fluidic component;
   a connecting device for fluidically connecting the fluidic port of the at least one component located in a testing position to a first adapter element of the connecting device; and
   a displacement device configured to displace the substrate and the connecting device relative to each other, and to bring the substrate into the testing position;
   wherein the connecting device further comprises a second adapter element arranged in an opposing position to the first adapter element with respect to the substrate in the testing position, wherein at least one of the first adapter element and the second adapter element is configured to be displaced towards the other element, so that the first adapter element and the second adapter element are brought into contact with the at least one fluidic component from opposite sides.

2. The test station according to claim 1, further comprising:
   a sensor device configured to measure a fluidic characteristic of the at least one fluidic component to be tested.

3. The test station according to claim 2, further comprising:
   a controller configured to control the sensor device to perform a measurement of the fluidic characteristic of the fluidic component to be tested for acquiring a sensor device output signal.

4. The test station according to claim 3, further comprising:
   a data processor for processing the sensor device output signal to acquire a processed data output signal representing the fluidic characteristic.

5. The test station according to claim 2, wherein the sensor device comprises a flow sensor, a pressure sensor, a mechanical sensor, a chemical sensor, a force sensor or an optical sensor.

6. The test station according to claim 1, wherein the first adapter element comprises an optical element or a contact element selected from a group comprising a fluidic contact element, an electrical contact element and a mechanical contact element.

7. The test station according to claim 1, wherein the second adapter element comprises an optical element or a contact element selected from a group comprising a fluidic contact element, an electrical contact element and a mechanical contact element.

8. The test station according to claim 1, wherein the first adapter element and the second adapter element each comprise a contact element selected from a group comprising a fluidic contact element, an electrical contact element and a mechanical contact element or an optical element, wherein the first adapter element and the second adapter element are of different types.

9. The test station according to claim 1, wherein the displacement device is configured to move the carrier device or the connecting device or both to bring the substrate into the testing position.

10. The test station according to claim 1, wherein the displacement device is configured to bring, in a first phase, a first fluidic component into the testing position, so that, in the first phase, the fluidic port of the first fluidic component is fluidically connected to the first adapter element and to bring, in a second phase, a second fluidic component into the testing position, so that, in the second phase, the fluidic port of the second fluidic component is fluidically connected to the first adapter element.

11. The test station according to claim 1, wherein the first adapter element is configured to simultaneously fluidically contact a group of neighboring fluidic components.

12. The test station according to claim 1, wherein the first adapter element is configured for fluidically contacting fluidic ports of each of the fluidic components simultaneously.

13. The test station according to claim 1, further comprising:
a controller configured to control the displacement device to perform a displacement of the substrate and the connecting device relative to each other for fluidically connecting, in the testing position, the fluidic port of the at least one fluidic component to the first adapter element.

14. The test station according to claim 1, wherein a plurality of fluidic components are arranged on the substrate.

15. The test station according to claim 1, wherein the at least one fluidic component comprises a micro pump, a valve, a fluid mixer, a drop dispenser, nozzle or a micro reactor.

16. The test station according to claim 1, wherein the at least one fluidic component is implemented as a MEMS element.

17. A method for testing at least one fluidic component arranged on a substrate, each fluidic component comprising a fluidic port, wherein the substrate with the at least one fluidic component is fixed in a holder, the method comprising:
bringing the substrate into a testing position;
in the testing position, fluidically connecting the fluidic port of the at least one fluidic components to a first adapter element;
arranging a second adapter element in an opposing position to the first adapter element with respect to the substrate in the testing position;
displacing the first adapter element and the second adapter element towards each other; and
bringing the first adapter element and the second adapter element into contact with the at least one fluidic component from opposite sides.

18. The method according to claim 17, further comprising:
measuring a fluidic characteristic of the at least one fluidic component to be tested.

19. A non-transitory computer-readable medium comprising a computer program comprising a program code for controlling a test station that performs a method for testing at least one fluidic component arranged on a substrate, each fluidic component comprising a fluidic port, wherein the substrate with the at least one fluidic component is fixed in a holder, when the computer program is executed on a computer and controls the test station, the method comprising:
bringing the substrate into a testing position;
in the testing position, fluidically connecting the fluidic port of the at least one fluidic components to a first adapter element;
arranging a second adapter element in an opposing position to the first adapter element with respect to the substrate in the testing position;
displacing the first adapter element and the second adapter element towards each other; and
bringing the first adapter element and the second adapter element into contact with the at least one fluidic component from opposite sides.

20. A test station for testing at least one fluidic component arranged on a substrate, each fluidic component comprising a fluidic port, the test station comprising:
a carrier device for holding the substrate with the at least one fluidic component;
a connecting device for fluidically connecting the fluidic port of the at least one component located in a testing position to a first adapter element of the connecting device; and
a displacement device configured to displace the substrate and the connecting device relative to each other, and to bring the substrate into the testing position;
wherein the first adapter element comprises a fluidic contact element and an electrical contact element.

21. A test station for testing at least one fluidic component arranged on a substrate, each fluidic component comprising a fluidic port, the test station comprising:
a carrier device for holding the substrate with the at least one fluidic component;
a connecting device for fluidically connecting the fluidic port of the at least one fluidic component located in a testing position to a first adapter element of the connecting device; and
a displacement device configured to displace the substrate and the connecting device relative to each other, and to bring the substrate into the testing position;
wherein the displacement device is configured to bring, in a first phase, a first group of fluidic components into the testing position, so that, in the first phase, fluidic ports of the first group of fluidic components are fluidically connected to the first adapter element and to bring, in a second phase, a second group of fluidic components into the testing position, so that, in the second phase, fluidic ports of the second group of fluidic components are fluidically connected to the first adapter element.

22. A test station for testing at least one fluidic component arranged on a substrate, each fluidic component comprising a fluidic port, the test station comprising:
a carrier device for holding the substrate with the at least one fluidic component;
a connecting device for fluidically connecting the fluidic port of the at least one component located in a testing position to a first adapter element of the connecting device; and
a displacement device configured to displace the substrate and the connecting device relative to each other, and to bring the substrate into the testing position;
wherein the first adapter element is configured to simultaneously fluidically contact a group of neighboring fluidic components.

23. A test station for testing at least one fluidic component arranged on a substrate, each fluidic component comprising a fluidic port, the test station comprising:
a carrier device for holding the substrate with the at least one fluidic component;
a connecting device for fluidically connecting the fluidic port of the at least one component located in a testing position to a first adapter element of the connecting device; and
a displacement device configured to displace the substrate and the connecting device relative to each other, and to bring the substrate into the testing position;
wherein the first adapter element is configured for fluidically contacting fluidic ports of each of the fluidic components simultaneously.

* * * * *